US009006421B2

(12) United States Patent
Lai et al.

(10) Patent No.: US 9,006,421 B2
(45) Date of Patent: Apr. 14, 2015

(54) CEPHALOSPORIN COMPOSITIONS AND METHODS OF MANUFACTURE

(71) Applicant: Cubist Pharmaceuticals, Inc., Lexington, MA (US)

(72) Inventors: Jan-Ji Lai, Westborough, MA (US); Pradip M. Pathare, Lexington, MA (US); Laxma Kolla, Princeton Jct., NJ (US); Adrien F. Soret, Brighton, MA (US)

(73) Assignee: Cubist Pharmaceuticals, Inc., Lexington, MA (US)

( * ) Notice: Subject to any disclaimer, the term of this patent is extended or adjusted under 35 U.S.C. 154(b) by 0 days.

(21) Appl. No.: 14/211,526

(22) Filed: Mar. 14, 2014

(65) Prior Publication Data

US 2014/0274958 A1    Sep. 18, 2014

Related U.S. Application Data

(60) Provisional application No. 61/782,365, filed on Mar. 14, 2013.

(51) Int. Cl.
| *C07D 501/06* | (2006.01) |
| *C07D 501/04* | (2006.01) |
| *C07F 9/6561* | (2006.01) |
| *A61K 31/546* | (2006.01) |
| *A61K 31/433* | (2006.01) |
| *A61K 31/426* | (2006.01) |
| *A61K 31/41* | (2006.01) |
| *A61K 31/545* | (2006.01) |

(52) U.S. Cl.
CPC .......... *C07D 501/06* (2013.01); *C07F 9/65613* (2013.01); *A61K 31/546* (2013.01); *C07D 501/04* (2013.01); *A61K 31/433* (2013.01); *A61K 31/426* (2013.01); *A61K 31/41* (2013.01); *A61K 31/545* (2013.01)

(58) Field of Classification Search
USPC ............ 514/80, 202, 206, 361; 540/215, 222, 540/225, 230
See application file for complete search history.

(56) References Cited

U.S. PATENT DOCUMENTS

| 3,980,644 A | 9/1976 | Lunn |
| 5,173,485 A | 12/1992 | Sakane et al. |
| 7,129,232 B2 | 10/2006 | Ohki et al. |

FOREIGN PATENT DOCUMENTS

| WO | 2005027909 A1 | 3/2005 |
| WO | 2013149121 A1 | 10/2013 |

OTHER PUBLICATIONS

International Search Report and Written Opinion of the International Searching Authority for International Application No. PCT/US2014/027706, dated Aug. 26, 2014 (12 pages).
Neu, Harold 'Relation of Structural Properties of Beta-Lactam Antibiotics to Antibacterial Activity'. The American Journal of Medicine. 1985, vol. 79, Suppl. 2A pp. 1-13.
Murano et al. 'Structural Requirements for the Stability of Novel Cephalosporins to AmpC beta-lactamase Based on 3D-Structure'. Bioorganic and Medicinal Chemistry. 2008, vol. 16, pp. 2261-2275.
Toda et al. 'Synthesis and SAR of Novel Parental Anti-psuedomonal cephalosporins Discovery of FR264205'. Bioorganic and Medicinal Chemistry Letters. 2008, vol. 18, pp. 4849-4852.
Ohki et al. 'Studies on 3'—Quaternary Ammonium Cephalosporins-III. Synthesis and Antibacterial Activity of 3'-(3-Aminopyrazolium)cephalosporins.' Bioorganic and Medicincal Chemistry. 1997, vol. 5, No. 3, pp. 557-567.
Ohki et al. 'Studies on 3'-Quaternary Ammonium Cephalosporins-IV. Synthesis and Antibacterial Activity of 3'(2-Alkyl-3-aminopyrazolium) cephalosporins Related to FK037'. Bioorganic and Medicincal Chemistry. 1997, vol. 5, No. 8, pp. 1685-1694.
Keltjens et al. 'A New Convenient Synthesis of 3-Carboxycephems Starting from 7-aminocephalosporanic Acid (7-ACA).' European Journal of Organic Chemistry. 2001, vol. 13, pp. 2529-2534.
Takeda et al. 'In Vitro and In Vivo Activities of a New Cephalosporins, FR264205, against *Pseudomonas aeruginosa*.' Antimicrobial Agents and Chemotherapy. 2007, vol. 51, No. 3, pp. 826-830.
Bryskier, Andre 'Cephems: Fifty Years of Continuous Research.' The Journal of Antibiotics. 2000, vol. 53, No. 10, pp. 1028-1037.
Neu, Harold 'Structure-Activity Relations of New beta-lactam Compounds and in Vitro Activity Against Common bacteria.' Reviews of Infectious Diseases. 1983, vol. 5, Suppl. 2, pp. S319-S337.

*Primary Examiner* — Kristin Vajda
(74) *Attorney, Agent, or Firm* — Lathrop & Gage LLP; Brian C. Trinque; David F. Cauble

(57) ABSTRACT

Provided herein is a method for the synthesis of cephalosporin antibiotic compounds comprising the conversion of a protected 7-amino group into a 7-carboxamide moiety in a single step.

16 Claims, 10 Drawing Sheets

7-carboxamide moiety    7-amino group

CEPHALOSPORIN COMPOSITIONS AND METHODS OF MANUFACTURE

RELATED APPLICATIONS

This application claims priority to U.S. Provisional Application No. 61/782,365, filed Mar. 14, 2013. The entire content of this application is incorporated herein by reference in its entirety.

TECHNICAL FIELD

The present disclosure relates to cephalosporin compositions and the manufacture thereof.

BACKGROUND

Cephalosporin compounds containing the chemical substructure of formula (I) are important antibacterial therapeutic agents. The manufacture of these cephalosporin compounds is typically performed in a series of synthetic chemical reactions. Reducing the number of synthetic chemical reactions and associated purification steps can increase product yield and decrease the time for production, thereby increasing efficiency and decreasing production costs.

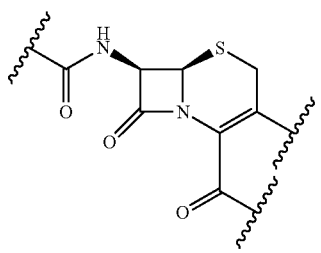

Syntheses of antibiotic cephalosporin compounds containing the substructure of formula (I) typically require two reactions for the formation of a 7-carboxamide moiety: (1) deprotection (i.e., removal of a protecting group) of the 7-amino group, and (2) acylation of the 7-amino group to form the 7-carboxamide moiety. One example of this two-step procedure is disclosed in U.S. Pat. No. 5,134,138 (see FIG. 2). Most cephalosporin antibiotics can be manufactured in an analogous way. Ceftolozane (CXA-101, FR264205) is a cephalosporin antibiotic compound, a synthesis of which is disclosed in U.S. Pat. No. 7,129,232. Additional cephalosporin antibiotic compounds include the compounds of Table 2. There remains an unmet need to identify novel manufacturing processes for synthesizing cephalosporin compounds comprising the chemical substructure of formula (I), including methods for formation of a 7-carboxamide moiety from a protected 7-amino group with fewer chemical synthetic steps.

SUMMARY

A novel chemical process useful in the manufacture of cephalosporin compounds containing the chemical substructure of Formula (I) can include deprotection (i.e., removal of a nitrogen protecting group) and acylation of the 7-amino group in a single step rather than multiple steps. The invention is based in part on the surprising discovery that salicylaldehyde imine derivatives according to formula (Ia) can be reacted with activated carboxylic acid derivatives (Ib) to yield 7-carboxamide compounds according to formula (I) in a single step. This outcome is surprising because the imine derivatives of formula (Ia) are stable to the reaction conditions in the absence of the activated carboxylic acid derivative.

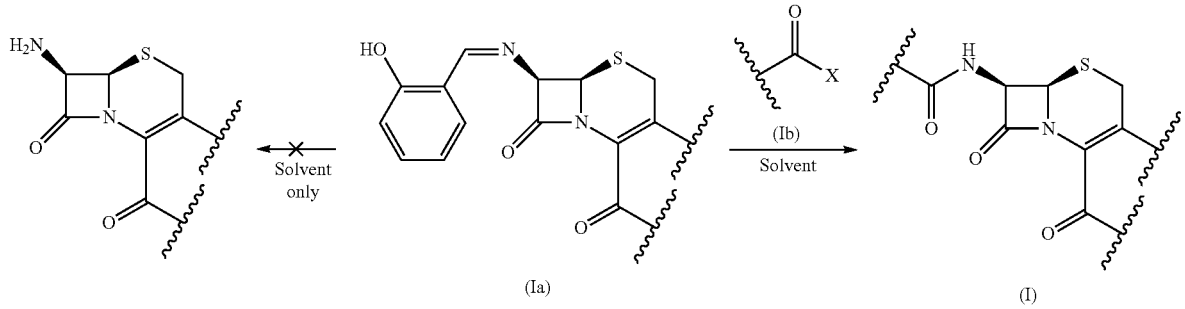

Accordingly, provided herein is a method for transforming a protected 7-amino group into a 7-carboxamide moiety comprising a single step.

DETAILED DESCRIPTION

Figure 1:
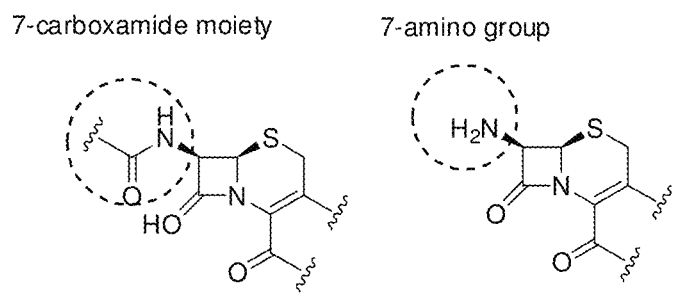
FIG. 1 depicts a representative 7-carboxamide moiety and 7-amino group.
Figure 2:
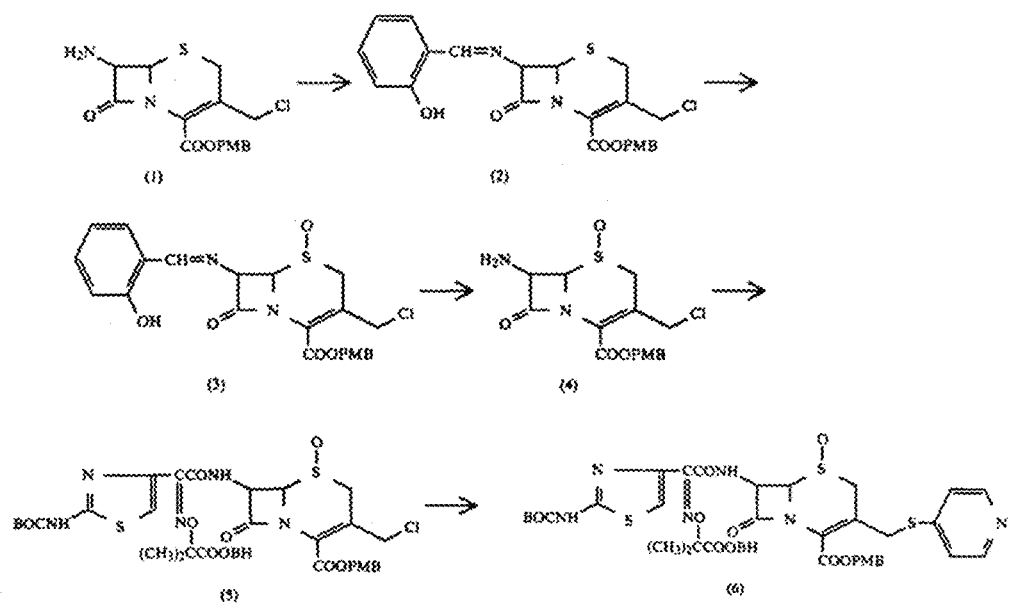
FIG. 2 depicts a prior art procedure (U.S. Pat. No. 5,134,138) comprising the deprotection of a protected 7-amino group followed by conversion of the 7-amino group into a 7-carboxamide moiety.
Figure 3:
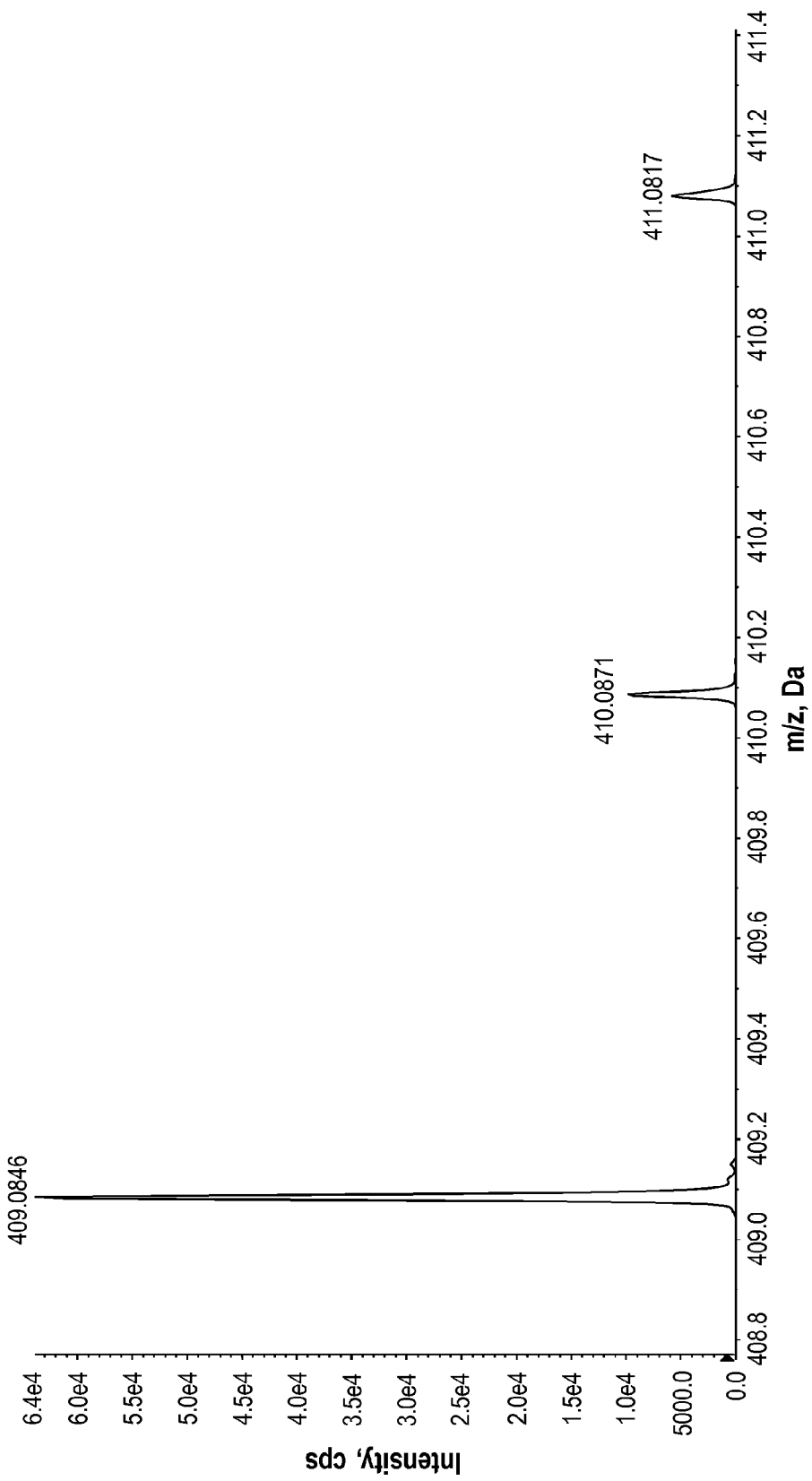
FIG. 3 depicts the full scan mass spectrum of compound (IV-1).
Figure 4:
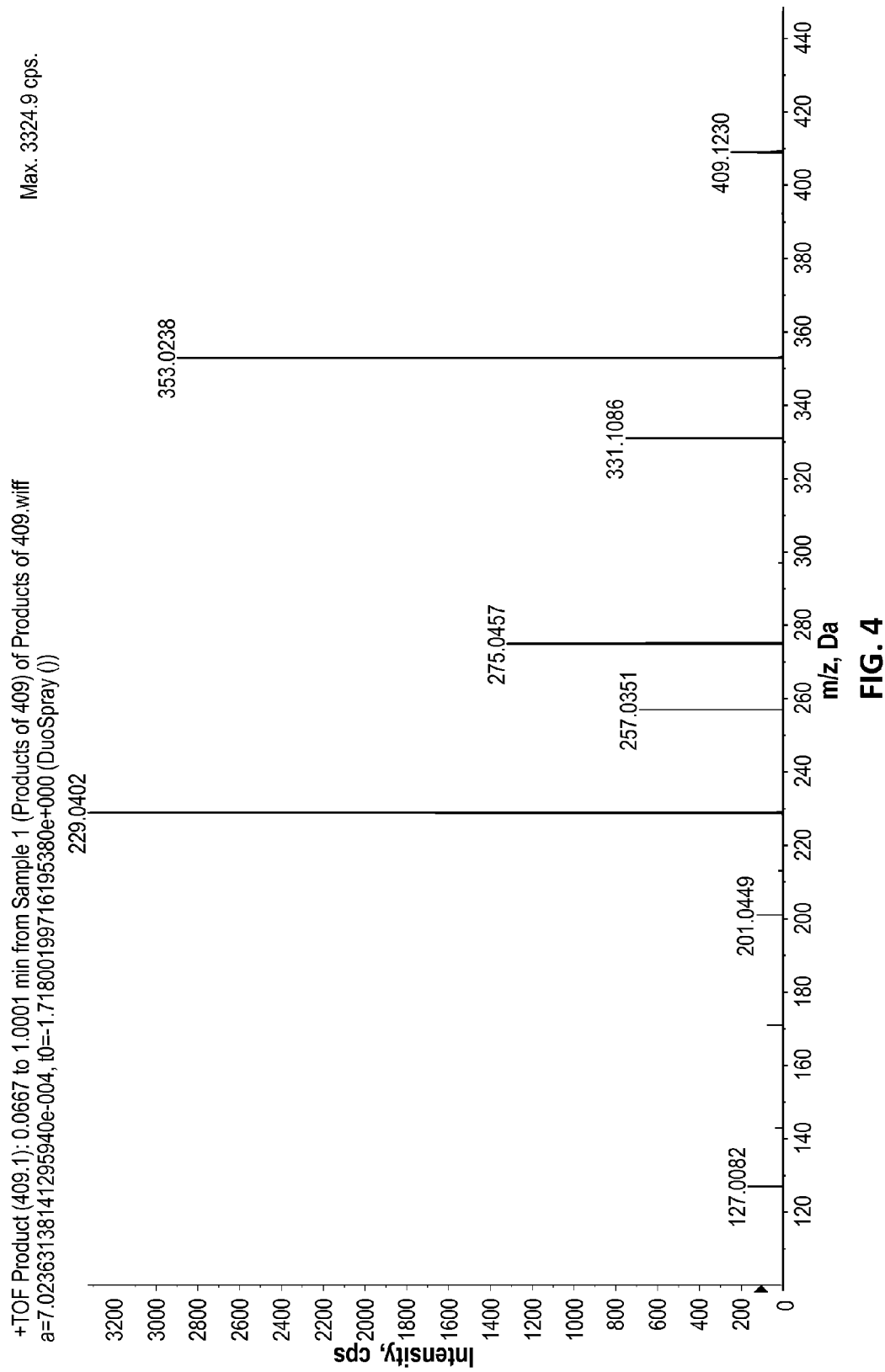
FIG. 4 depicts the product ion mass spectrum of compound (IV-1).
Figure 5:
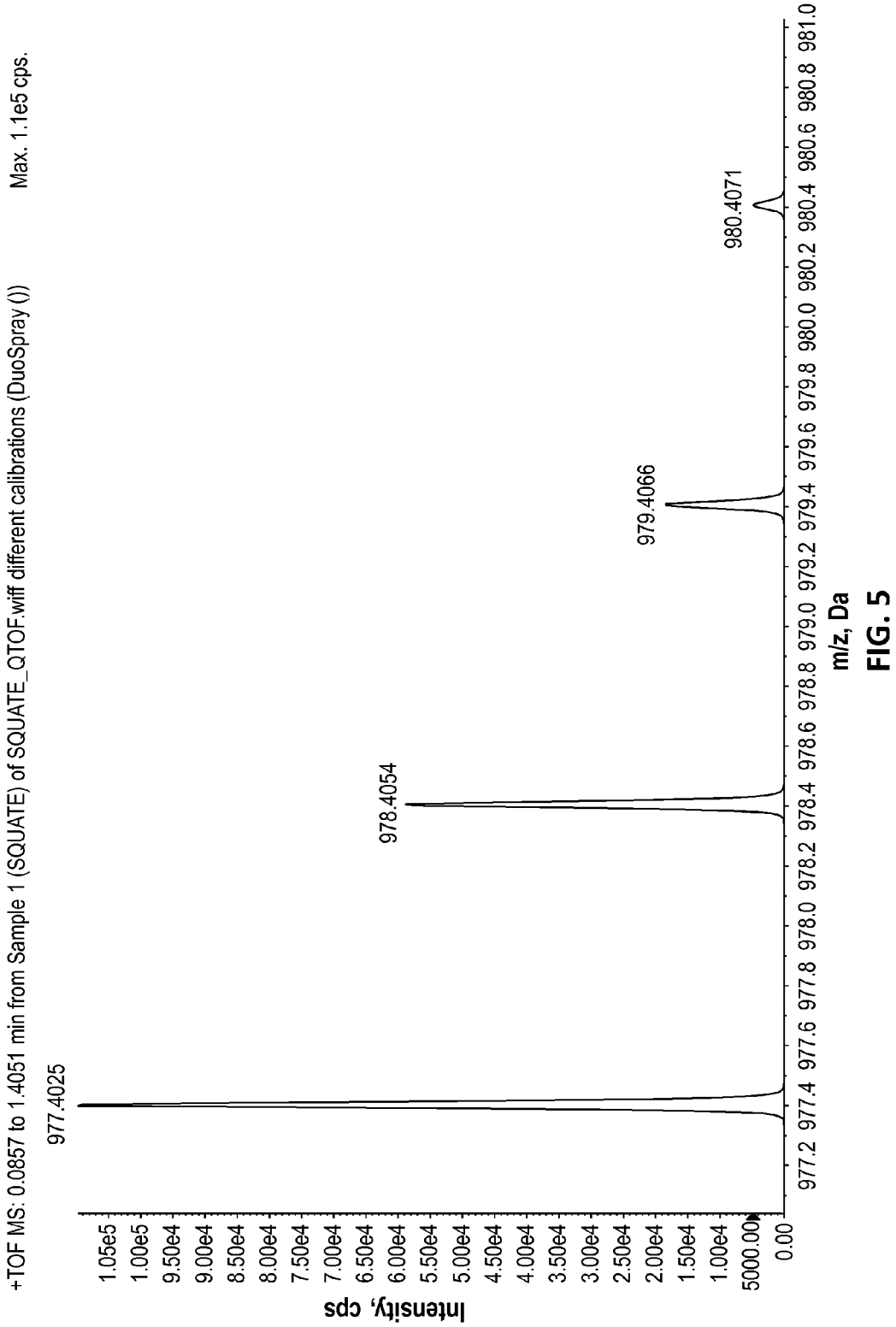
FIG. 5 depicts the full scan mass spectrum of compound (III-1).
Figure 6:
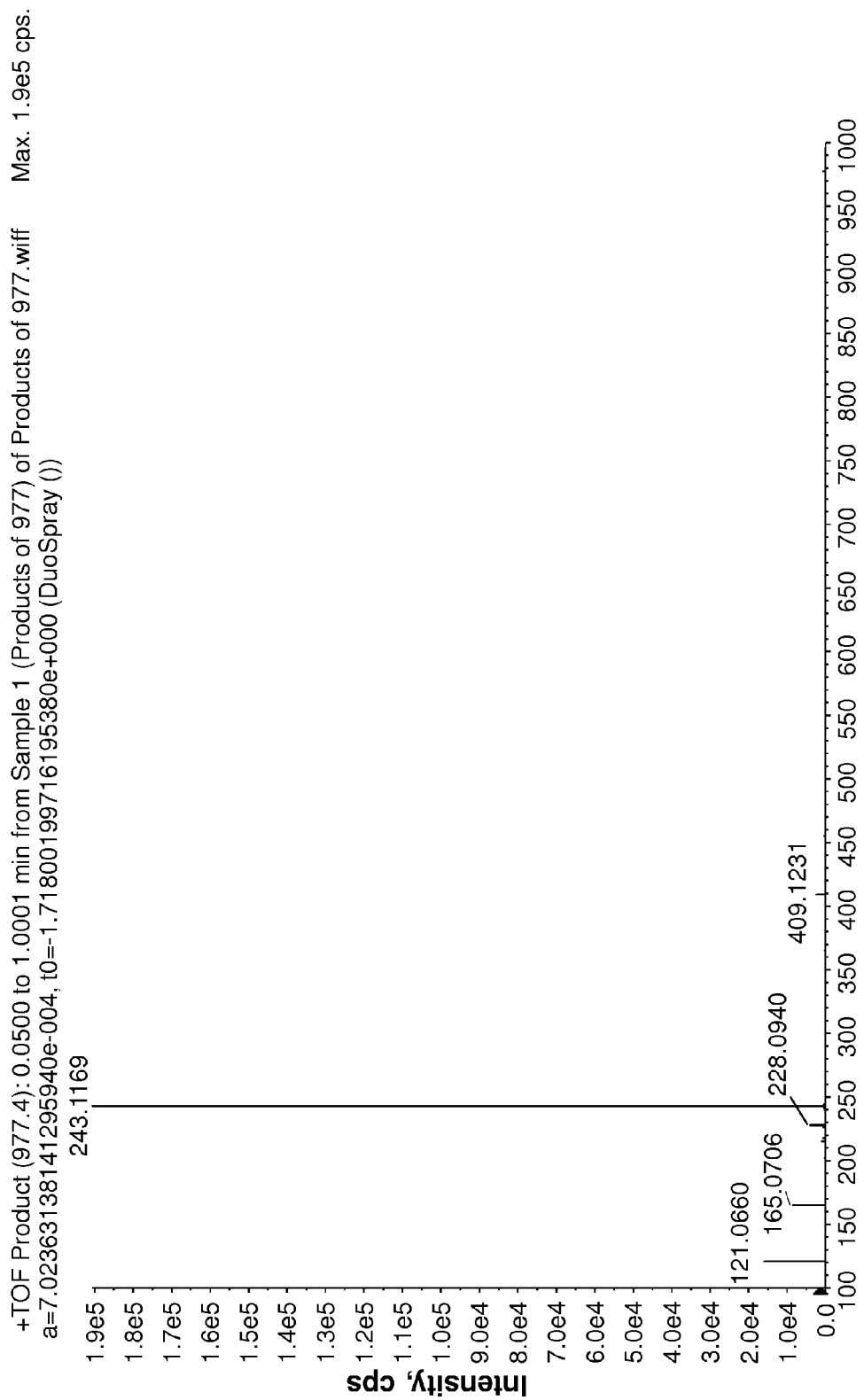
FIG. 6 depicts the product ion mass spectrum of compound (III-1).
Figure 7:
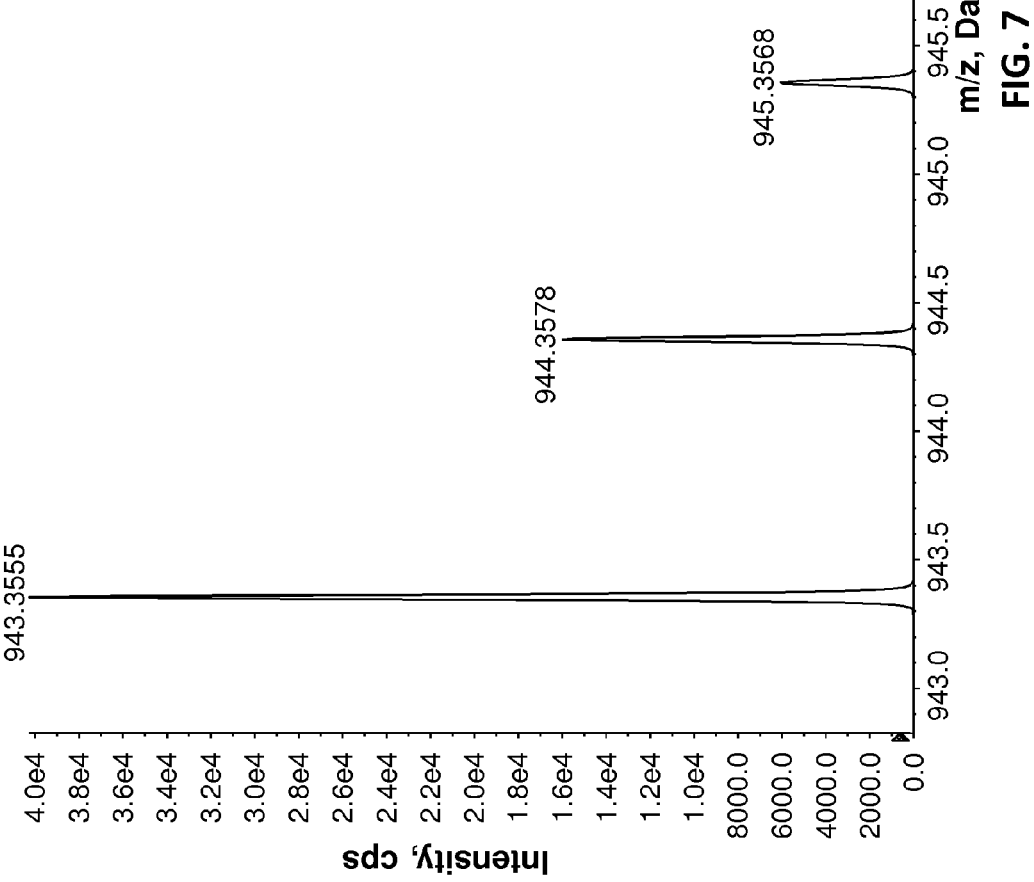
FIG. 7 depicts the full scan mass spectrum of compound (II-1).
Figure 8:
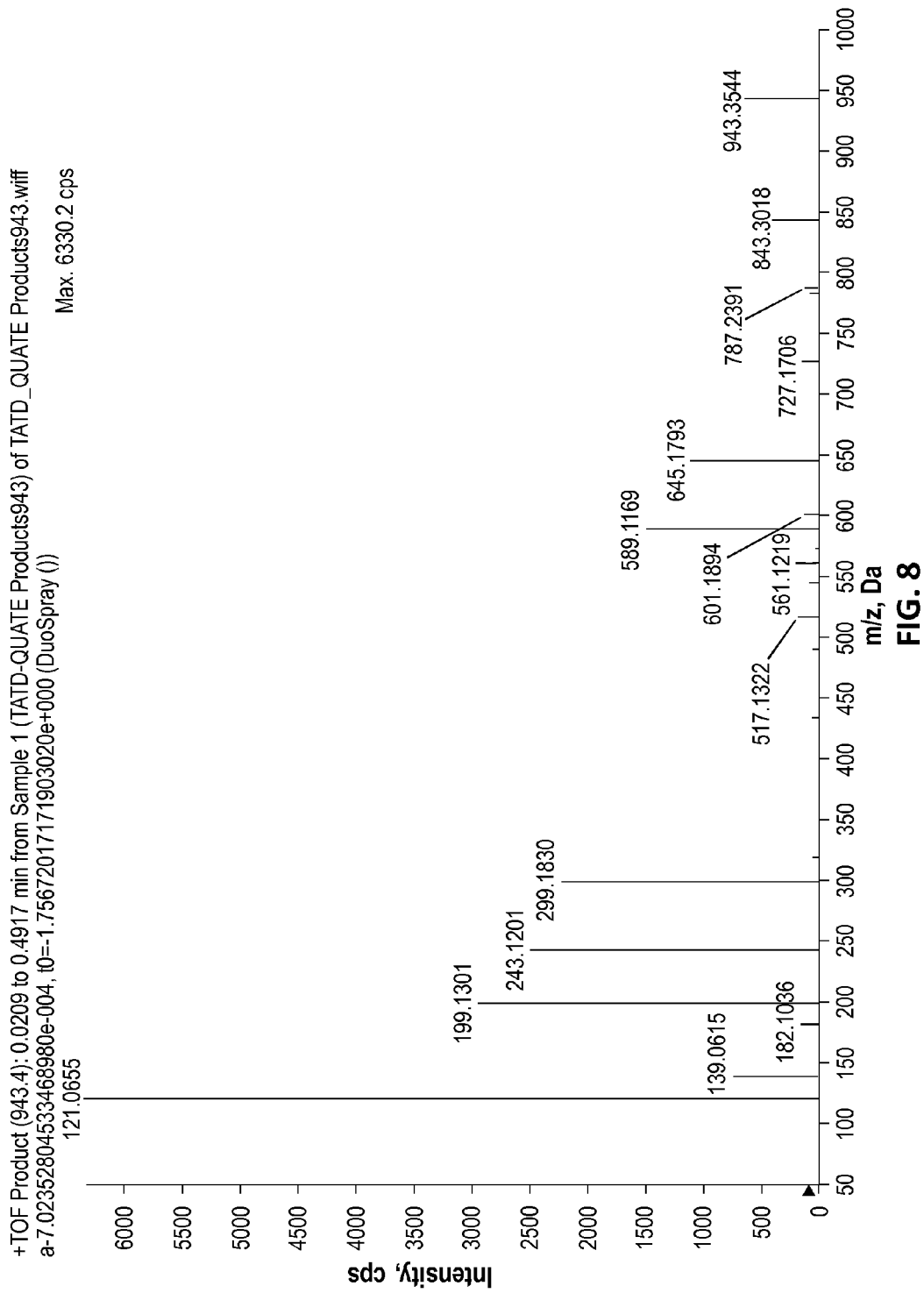
FIG. 8 depicts the product ion mass spectrum of compound (II-1).
Figure 9:
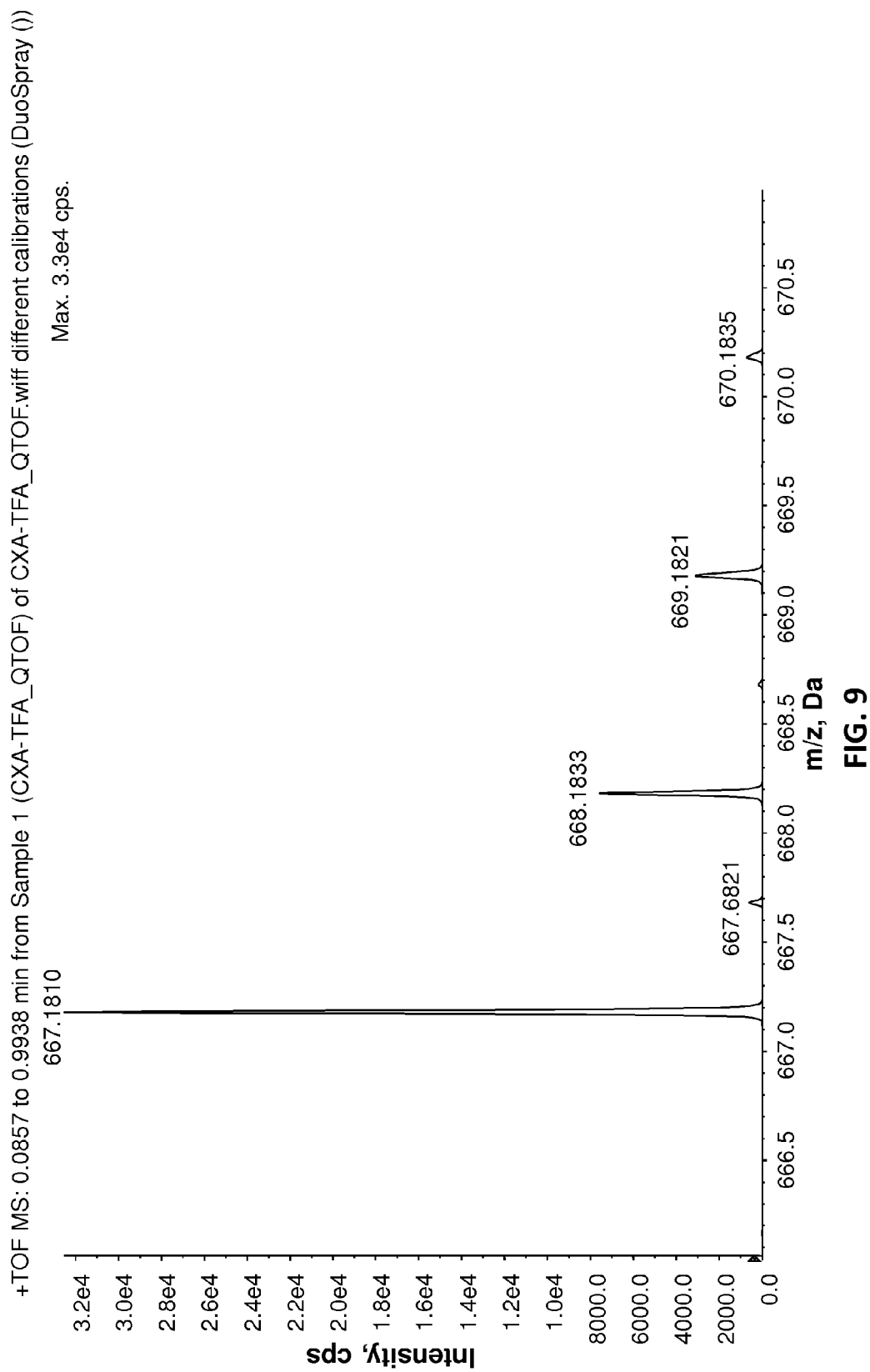
FIG. 9 depicts the full scan mass spectrum of ceftolozane trifluoroacetate.
Figure 10:
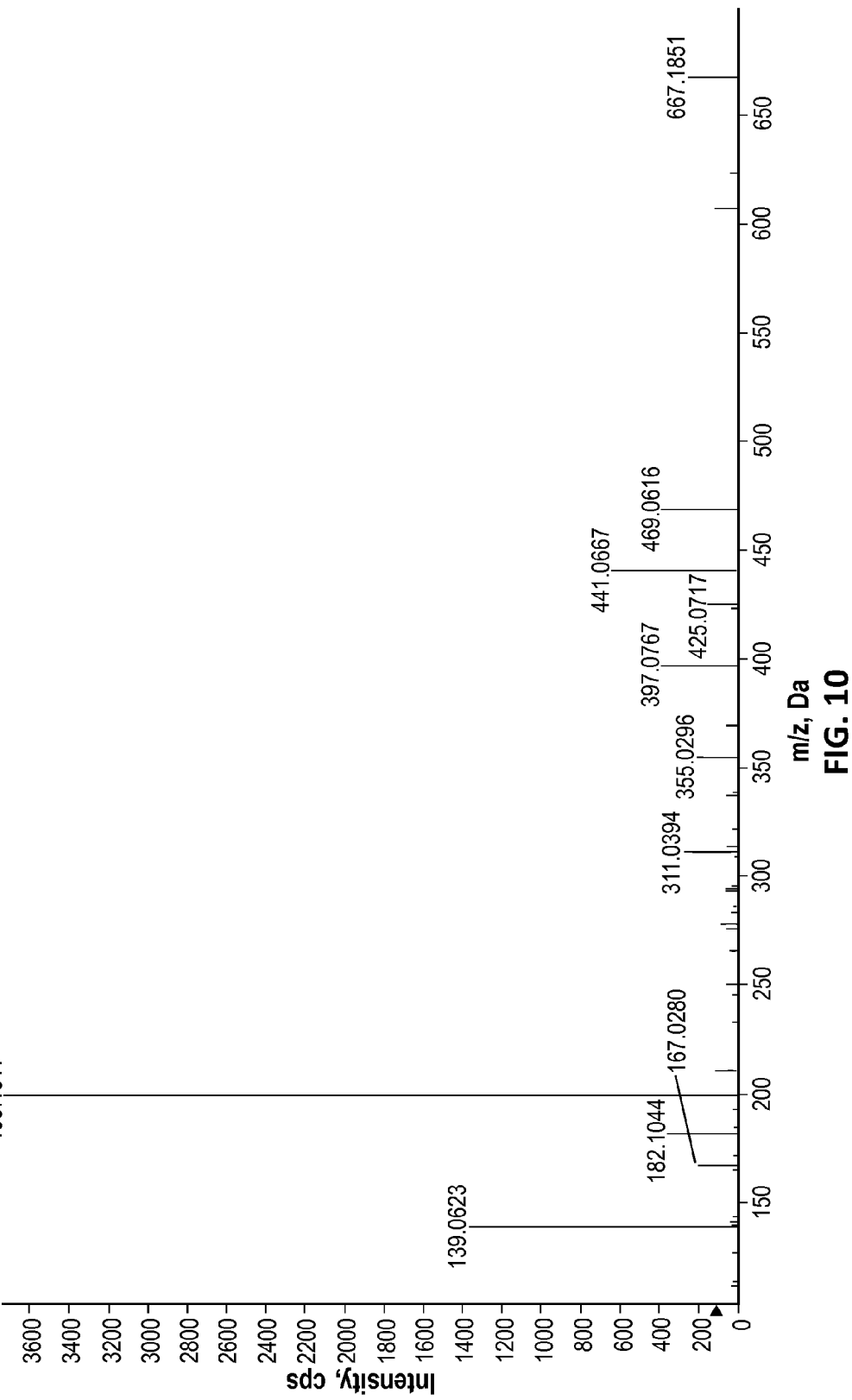
FIG. 10 depicts the product ion mass spectrum of ceftolozane trifluoroacetate.

Provided herein is a method for preparing a compound of formula (II), or a salt thereof, comprising the step of reacting a compound of formula (III), or a salt thereof, with a compound of formula (IV), or a salt thereof, under suitable conditions to form a compound of formula (II), or a salt thereof, wherein the compounds of formulas (II), (III) and (IV) are defined according to the variable values below.

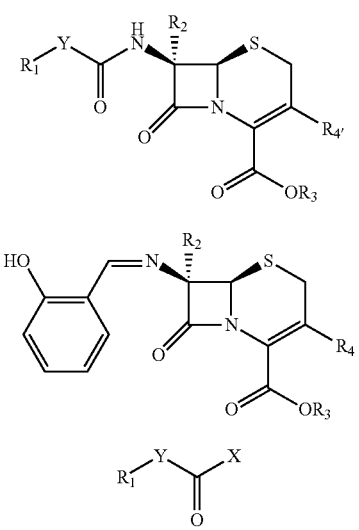

Variable $R_1$

In certain embodiments, $R_1$ is $R_1'$—Z; wherein $R_1'$ is selected from the group consisting of a bond, aryl, cycloalkyl, cycloalkenyl, heterocyclyl, and heteroaryl; wherein Z is 0-2 instances of a substituent that for each occurrence is independently selected from the group consisting of hydrogen, halogen, hydroxyl, hydroxyalkyl, aminoalkyl, alkyl, alkylidenyl, alkenyl, heteroalkyl, cyano and amino, wherein Z is optionally, independently substituted one or more times with amino, halogen, carboxyl, carboxamide, oxo, a nitrogen protecting group, an oxygen protecting group or —P(O)(OZ')$_2$; and wherein Z' is independently hydrogen or an oxygen protecting group.

In one embodiment, $R_1$ is selected from the group consisting of aryl and heteroaryl moieties. In certain embodiments, $R_1$ is a substituted or unsubstituted aryl or heteroaryl moiety selected from the group consisting of: thiophene, furan, thiazole, tetrazole, thiadiazole, pyridyl, phenyl, phenol, cyclohexadiene and dithietane. In a particular embodiment, $R_1$ is selected from the group consisting of the following moieties:

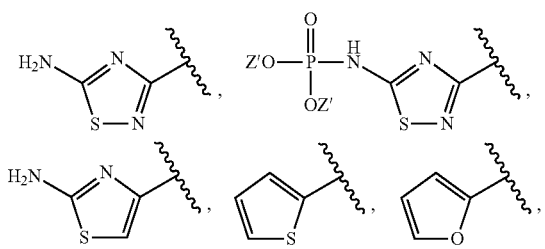

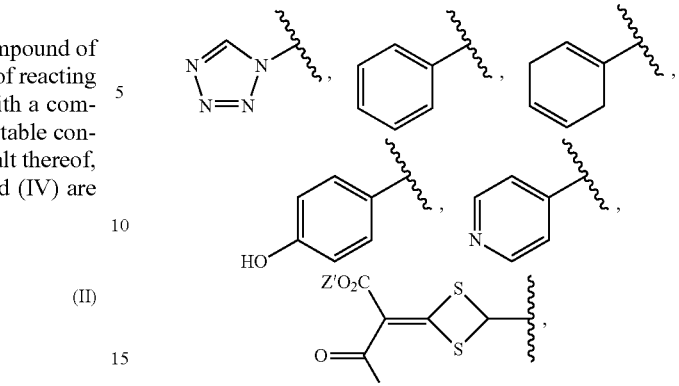

and salts thereof, wherein Z' is defined above.

In a particular embodiment, $R_1$ is and the compound of formula (II) has the structure of formula (IIa).

Variable $R_2$

In certain embodiments, $R_2$ is selected from the group consisting of hydrogen and alkoxy. In another embodiment of the method, $R_2$ is hydrogen, and the compound of formula (II) has the structure of formula (IIb).

Variable Y

In certain embodiments, Y is selected from the group consisting of a bond, CH$_2$, CH$_2$S, SCH$_2$, C=C(H)CH$_2$CO$_2$R', CH(OR'), C=N(OR'), CHNR"$_2$ and C=NR"; wherein R' is selected from the group consisting of hydrogen, an oxygen protecting group and alkyl, wherein the alkyl is optionally substituted one or more times with halogen, hydroxyl or —CO$_2$R$_5$; wherein R" is a substituent that for each occurrence is selected from hydrogen, alkyl, C(O)heterocyclyl, and a nitrogen protecting group, wherein any two R" substituents may combine to form a ring or a single nitrogen protecting group; and wherein $R_5$ is independently hydrogen or an oxygen protecting group.

In one embodiment of the method, Y is selected from a bond, $CH_2$, $CH_2S$ and $C=C(H)CH_2CO_2R'$, and R' is selected from the group consisting of hydrogen and an oxygen protecting group. In another embodiment, Y is $C=N(OR')$ and R' is selected from the group consisting of an oxygen protecting group, hydrogen, methyl, ethyl, $CH_2CO_2R_5$ and $C(CH_3)_2CO_2R_5$. In yet another embodiment, Y is $CH(OR')$ and R' is hydrogen or an oxygen protecting group. In still another embodiment, Y is $CHNR''_2$ and R" is 1-2 instances of a substituent that for each occurrence is selected from hydrogen, a nitrogen protecting group and

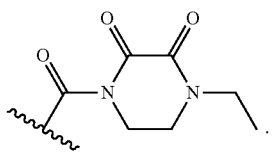 [SMILES: *C(=O)N1CCN(CC)C(=O)C1=O]

In a particular embodiment, Y is $C=N(OR')$ and R' is $C(CH_3)_2 CO_2{}^tBu$, and the compound of formula (II) has the structure of formula (IIc).

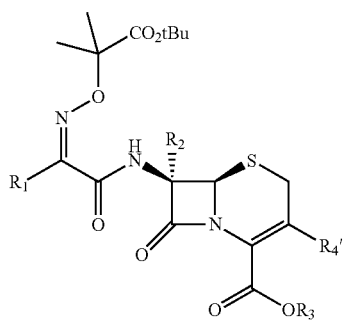

(IIc)

Variable $R_3$

In certain embodiments, $R_3$ is selected from the group consisting of hydrogen and an oxygen protecting group. In another embodiment of the method, $R_3$ is an oxygen protecting group selected from benzyl ethers. Benzyl ethers may be substituted (e.g., with one or more alkoxy substituents) or unsubstituted. In a particular embodiment, $R_3$ is

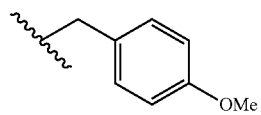 [SMILES: *Cc1ccc(OC)cc1]

(i.e., 4-methoxybenzyl, PMB, MPM).

Variables $R_4$ and $R_{4'}$ $R_4$ and $R_{4'}$ are independently selected from the group consisting of halogen, $-R_6-R_7$, $-CH_2-R_6-R_7$ and $-CH=R_7$; wherein $R_6$ is selected from the group consisting of a bond, oxygen, sulfur, alkyl, alkenyl, aryl, heteroaryl and heterocyclyl; wherein $R_7$ is selected from the group consisting of hydrogen, alkyl, alkenyl, alkanoyl, aroyl, heteroaroyl, carboxamide, aryl, heteroaryl and heterocyclyl; and wherein $R_7$ is optionally, independently substituted 1-3 times with a substituent selected from alkyl, alkyl sulfite, heterocyclyl and $NR_aR_b$; wherein $R_a$ and $R_b$ are independently selected from the group consisting of hydrogen, alkyl, a nitrogen protecting group and $C(O)NHR_c$; wherein $R_c$ is an alkyl group or a heteroalkyl group; and wherein $R_4$ and $R_{4'}$ are optionally, independently substituted one or more times with an oxygen protecting group or a nitrogen protecting group.

In another embodiment of the method, $R_4$ and $R_{4'}$ are independently selected from the group consisting of hydrogen, chlorine, methyl, $CH=CH-CH_3$, $CH=CH_2$, $CH_2OC(O)CH_3$, $CH_2OC(O)NH_2$, $CH_2OCH_3$,

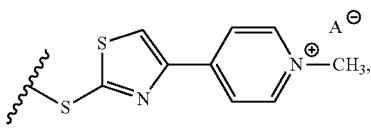

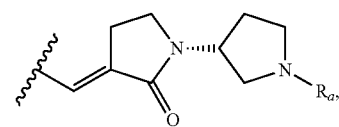

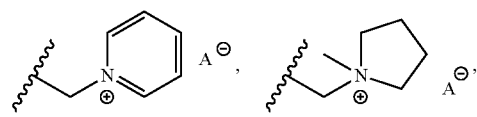

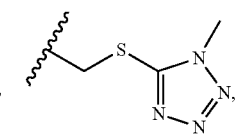

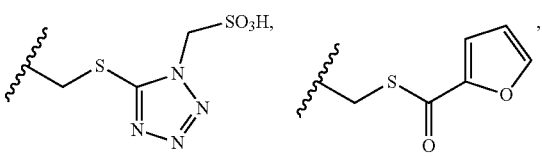

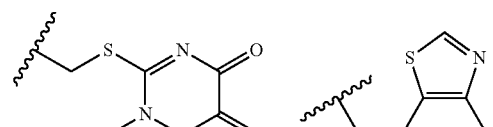

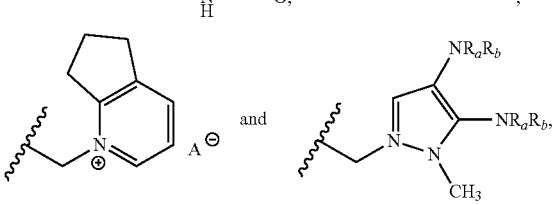

and wherein $A^\ominus$, for each occurrence, is independently a pharmaceutically acceptable anion. In certain embodiments, $A^\ominus$ is selected from chloride, acetate, trifluoroacetate and bisulfate. In a particular embodiment, $A^\ominus$ is trifluoroacetate.

In a particular embodiment, $R_4$ is

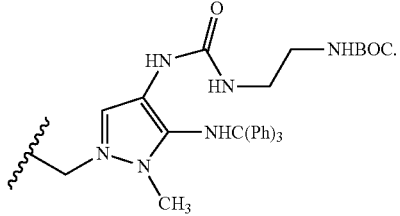

In another particular embodiment, $R_{4'}$ is

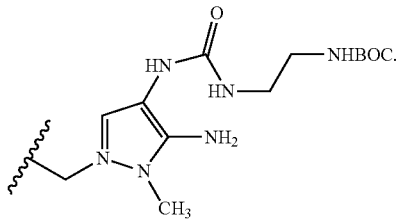

Variable X

In certain embodiments, X is selected from the group consisting of halogen, —OC(O)$R_8$ and —OSO$_2R_8$; wherein $R_8$ is selected from the group consisting of alkyl, heteroalkyl, aryl and heteroaryl. In another embodiment of the method, X is —OSO$_2R_8$. In a particular embodiment, X is —OSO$_2$CH$_3$.

METHODS OF THE INVENTION

In one aspect, provided herein is a method for preparing a compound of formula (II), or a salt thereof,

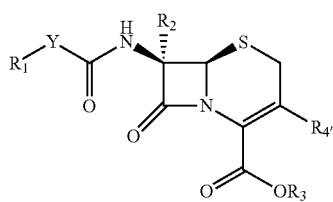

comprising the step of reacting a compound of formula (III), or a salt thereof,

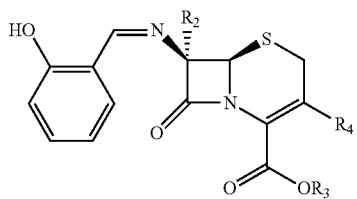

with a compound of formula (IV), or a salt thereof,

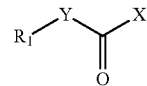

in a mixture comprising an organic solvent and water, to form a compound of formula (II), or a salt thereof; wherein:

$R_1$ is $R_{1'}$—Z, wherein $R_{1'}$ is selected from the group consisting of a bond, aryl, cycloalkyl, cycloalkenyl, heterocyclyl, and heteroaryl; and Z is 0-2 instances of a substituent that for each occurrence is independently selected from the group consisting of hydrogen, halogen, hydroxyl, hydroxyalkyl, aminoalkyl, alkyl, alkylidenyl, alkenyl, heteroalkyl, cyano and amino, wherein Z is optionally, independently substituted one or more times with amino, halogen, carboxyl, carboxamido, oxo, a nitrogen protecting group, an oxygen protecting group or —P(O)(OZ')$_2$; and wherein Z' is independently hydrogen or an oxygen protecting group;

Y is selected from the group consisting of a bond, CH$_2$, CH$_2$S, SCH$_2$, C=C(H)CH$_2$CO$_2$R', CH(OR'), C=N(OR'), CHNR"$_2$ and C=NR"; wherein R' is selected from the group consisting of hydrogen, an oxygen protecting group and alkyl, wherein the alkyl is optionally substituted one or more times with halogen, hydroxyl or —CO$_2R_5$, and wherein $R_5$ is independently hydrogen or an oxygen protecting group; and wherein R" is a substituent that for each occurrence is selected from hydrogen, alkyl, C(O)heterocyclyl, and a nitrogen protecting group, wherein any two R" substituents may combine to form a ring or a single nitrogen protecting group;

$R_2$ is selected from the group consisting of hydrogen and alkoxy;

$R_3$ is selected from the group consisting of hydrogen and an oxygen protecting group; and $R_4$ and $R_{4'}$ are each independently selected from the group consisting of halogen, —$R_5$—$R_7$, —CH$_2$—$R_5$—$R_7$ and —CH=$R_7$; wherein $R_4$ and $R_{4'}$ are optionally, independently substituted one or more times with an oxygen protecting group or a nitrogen protecting group;

$R_6$ is selected from the group consisting of a bond, oxygen, sulfur, alkyl, alkenyl, aryl, heteroaryl and heterocyclyl;

$R_7$ is selected from the group consisting of hydrogen, alkyl, alkenyl, alkanoyl, aroyl, heteroaroyl, carboxamide, aryl, heteroaryl and heterocyclyl; and wherein $R_7$ is optionally, independently substituted 1-3 times with a substituent selected from alkyl, alkyl sulfite, heterocyclyl and NR$_a$R$_b$; wherein $R_a$ and $R_b$ are independently selected from the group consisting of hydrogen, alkyl and C(O)NHR$_c$;

$R_c$ is alkyl or heteroalkyl; and wherein

X is selected from the group consisting of halogen, —OC(O)$R_8$ and —OSO$_2R_8$, wherein $R_8$ is selected from the group consisting of alkyl, heteroalkyl, aryl and heteroaryl.

In one embodiment of the method, $R_1$ is selected from the group consisting of:

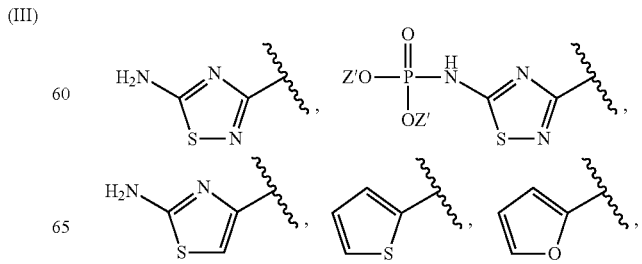

-continued

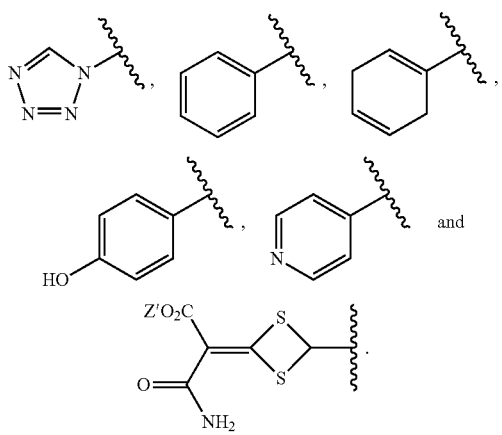

In another embodiment of the method, $R_2$ is hydrogen.

In another embodiment of the method, Y is selected from a bond, $CH_2$, $CH_2S$ and $C=C(H)CH_2CO_2R'$ and R' is selected from the group consisting of hydrogen and an oxygen protecting group, or wherein Y is $C=N(OR')$ and R' is selected from the group consisting of an oxygen protecting group, hydrogen, methyl, ethyl, $CH_2CO_2R_5$ and $C(CH_3)_2CO_2R_5$ and $R_5$ is hydrogen or an oxygen protecting group, or wherein Y is CH(OR') and R' is hydrogen or an oxygen protecting group, or wherein Y is $CHNR''_2$ and R" is 1-2 instances of a substituent that for each occurrence is selected from hydrogen, a nitrogen protecting group and

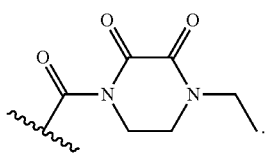 [SMILES: *C(=O)N1CCN(CC)C(=O)C1=O]

In another embodiment of the method, $R_3$ is an oxygen protecting group that is a benzyl ether. In a particular embodiment, $R_3$ is paramethoxybenzyl (PMB).

In another embodiment of the method, $R_4$ and $R_4$, are selected from the group consisting of hydrogen, chlorine, methyl, $CH=CH-CH_3$, $CH=CH_2$, $CH_2OC(O)CH_3$, $CH_2OC(O)NH_2$, $CH_2OCH_3$,

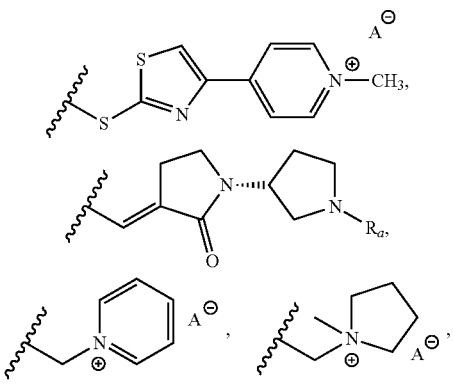

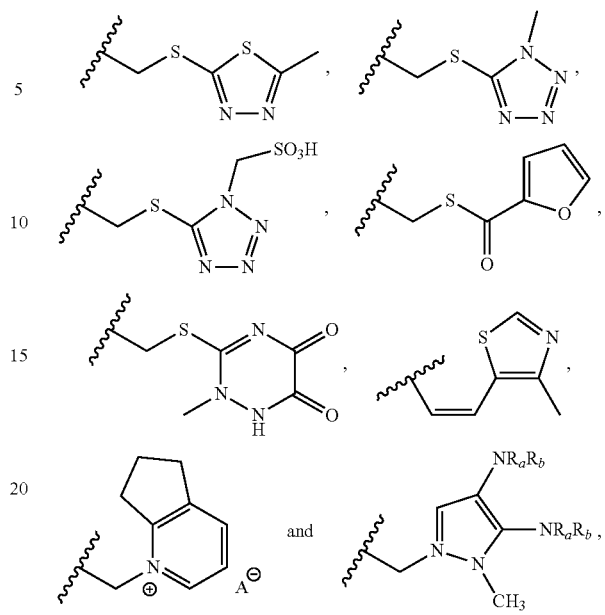

wherein each occurrence of $A^\ominus$ is independently an anion.

In another aspect, provided herein is a method for preparing a compound of formula (II), or a salt thereof,

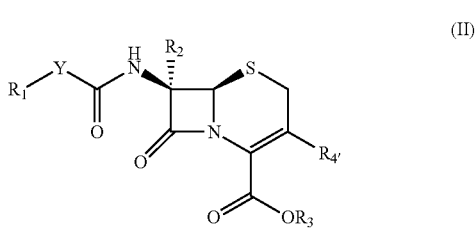
(II)

comprising the step of reacting a compound of formula (III), or a salt thereof,

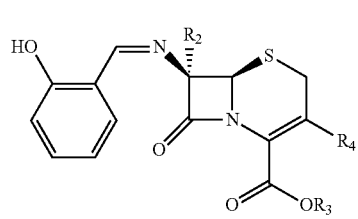
(III)

with a compound of formula (IV), or a salt thereof,

(IV)

in a mixture comprising an organic solvent and water, to form a compound of formula (II), or a salt thereof; wherein:

$R_1$ is selected from the group consisting of:

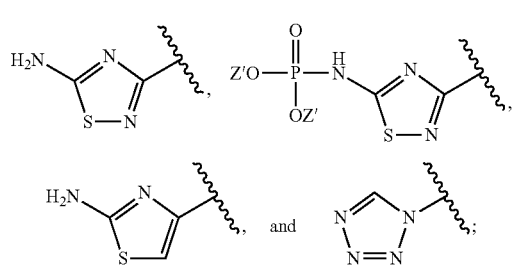

wherein Z' is independently hydrogen or an oxygen protecting group;

Y is selected from the group consisting of:

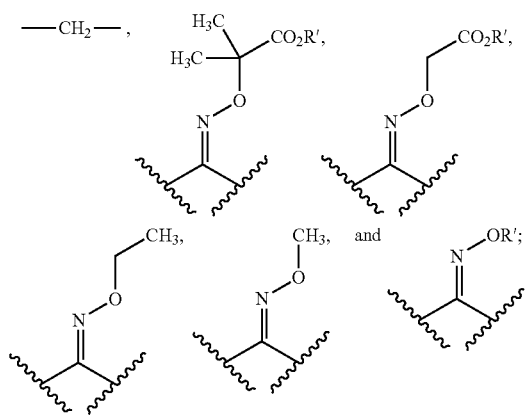

wherein R' is selected from the group consisting of hydrogen and an oxygen protecting group;

$R_2$ is hydrogen;

$R_3$ is selected from the group consisting of hydrogen and an oxygen protecting group; and $R_4$ and $R_{4'}$ are each independently selected from the group consisting of:

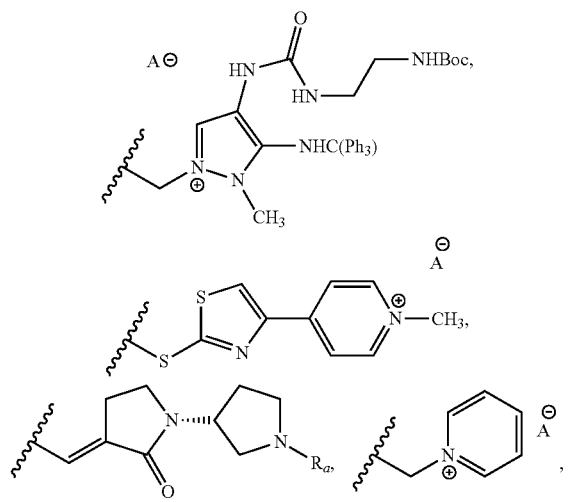

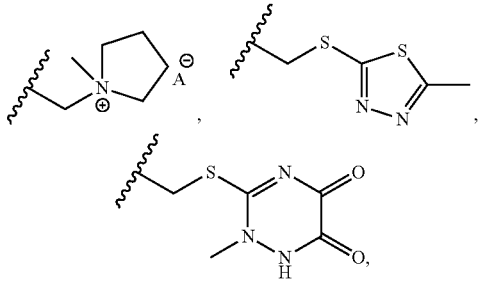

and —CH=$CH_2$, wherein each occurrence of $A^{\ominus}$ is independently an anion, and X is —$OSO_2R_8$, wherein $R_8$ is selected from the group consisting of alkyl, heteroalkyl, aryl and heteroaryl.

In one embodiment of the above methods, further comprises the step of reacting the compound of formula (II), or a salt thereof, with a strong acid to form a compound of formula (V), or a salt thereof, wherein the compound of formula (V) is selected from the compounds of Table 2. The strong acid can be a Bronsted acid (e.g., trifluoroacetic acid, hydrochloric acid), or a Lewis acid (e.g., $TiCl_4$). In a particular embodiment, the strong acid is trifluoroacetic acid.

Also provided herein are particular embodiments of the method (a)-(h), wherein:

(a) the compound of formula (III) has the structure:

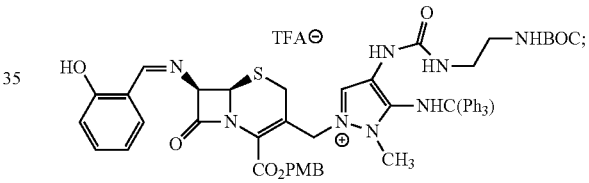

the compound of formula (II) has the structure:

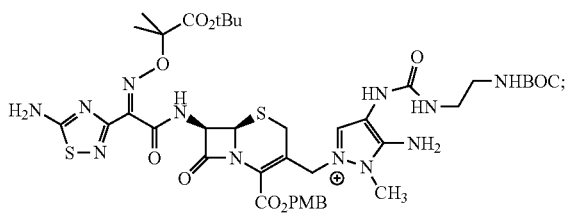

and
the compound of formula (V) has the structure:

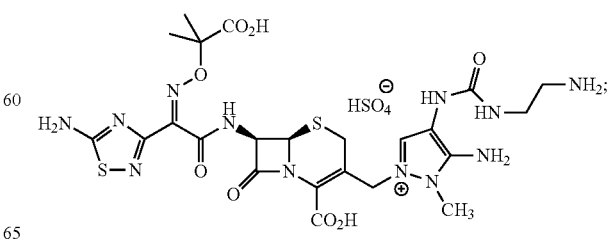

(b) the compound of formula (III) has the structure:
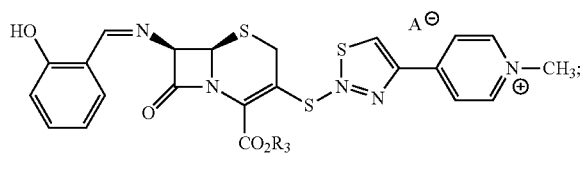
the compound of formula (II) has the structure:
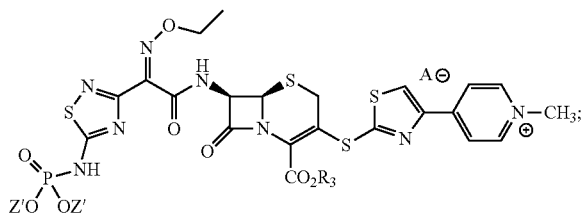
and
the compound of formula (V) has the structure:
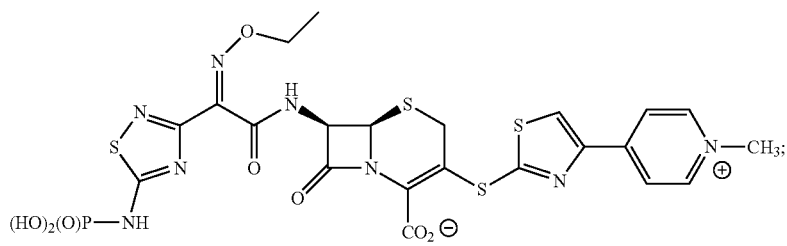
(c) the compound of formula (III) has the structure:
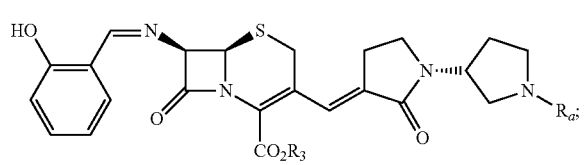
the compound of formula (II) has the structure:
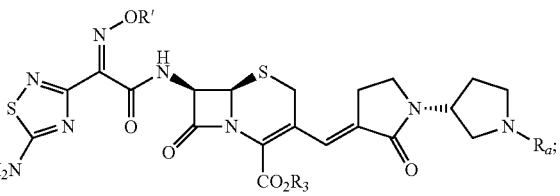
and
the compound of formula (V) has the structure:
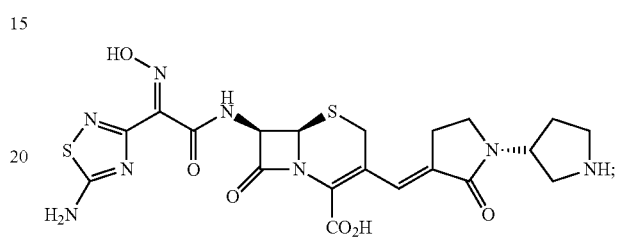
(d) the compound of formula (III) has the structure:
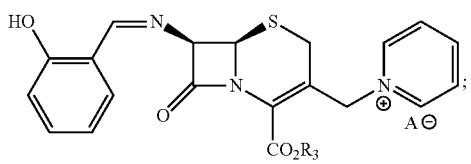

the compound of formula (II) has the structure:

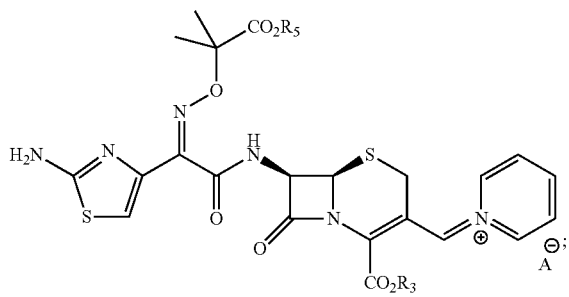

and
the compound of formula (V) has the structure:

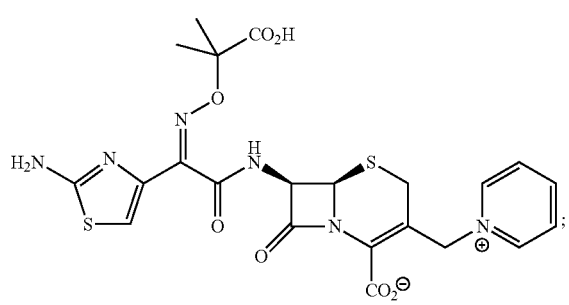

(e) the compound of formula (III) has the structure:

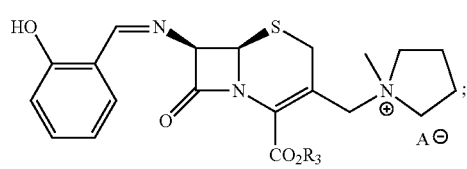

the compound of formula (II) has the structure:

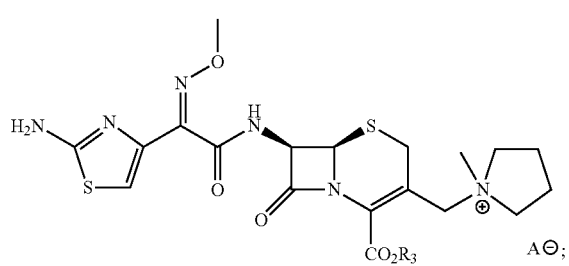

and
the compound of formula (V) has the structure:

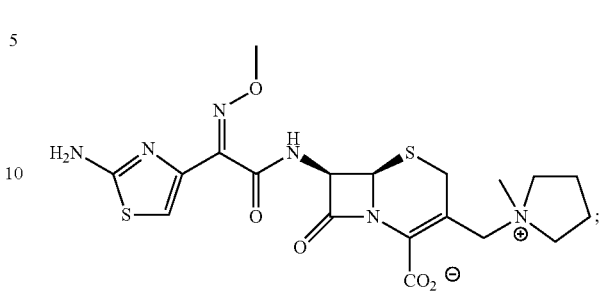

(f) the compound of formula (III) has the structure:

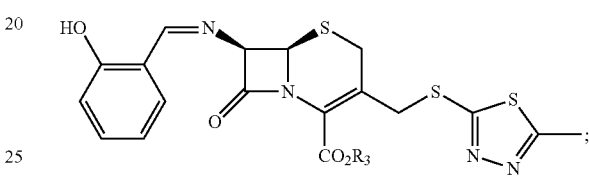

the compound of formula (II) has the structure:

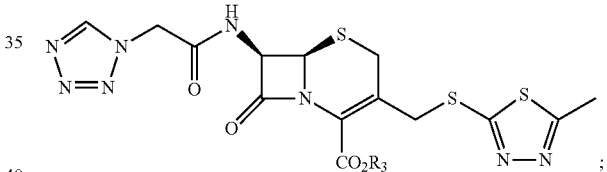

and
the compound of formula (V) has the structure:

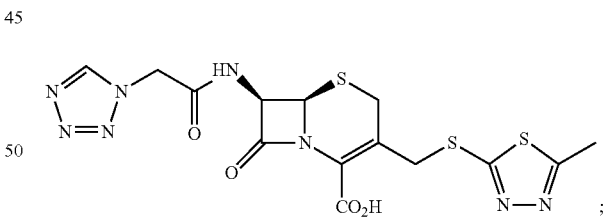

(g) wherein the compound of formula (III) has the structure:

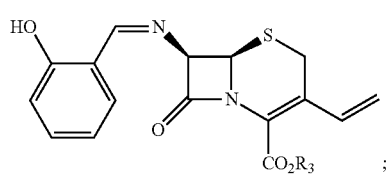

the compound of formula (II) has the structure:

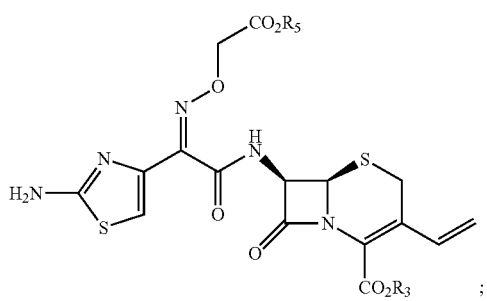

and the compound of formula (V) has the structure:

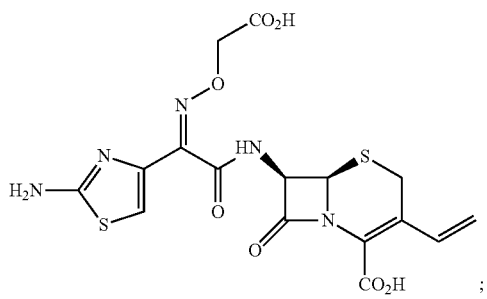 [SMILES: C=CC1=C(C(=O)O)N2C(=O)[C@@H](NC(=O)/C(=N\OCC(=O)O)c3csc(N)n3)[C@H]2SC1]

and (h) the compound of formula (III) has the structure:

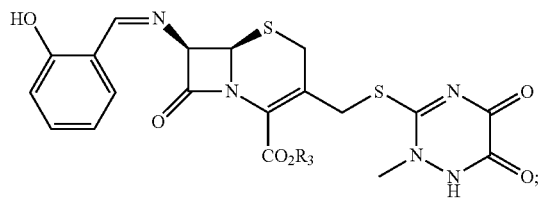

the compound of formula (II) has the structure:

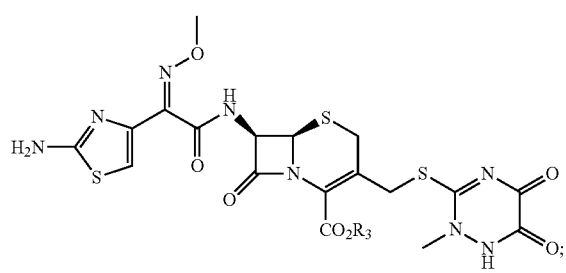

and the compound of formula (V) has the structure:

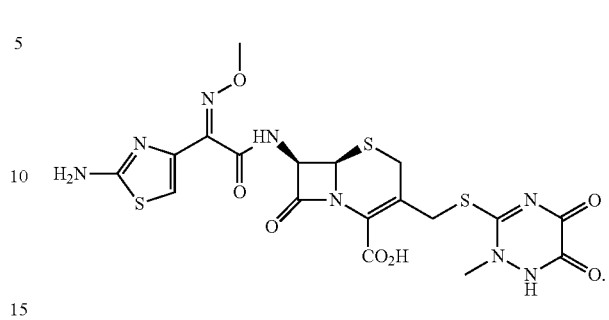

Compositions

In another aspect, provided herein is a composition comprising the compound of formula (V), or salt a thereof, and one or more compound selected from the group consisting of: the compound of formula (II), or salt a thereof, the compound of formula (III), or salt a thereof, and the compound of formula (IV), or salt a thereof. In one embodiment, the composition comprises the compound of formula (V), or salt a thereof, the compound of formula (I) or salt a thereof, the compound of formula (Ia) or salt a thereof, and the compound of formula (Ib) or salt a thereof. In another embodiment of the composition, the compound of formula (II), or salt a thereof, the compound of formula (III), or salt a thereof, and the compound of formula (IV), or salt a thereof, are present, if at all, in an amount that is less than or equal to 0.05% w/w. In yet another embodiment of the composition, the compound of formula (II), or salt a thereof, the compound of formula (III), or salt a thereof, and the compound of formula (IV), or salt a thereof, are present, if at all, in an amount that is less than or equal to 0.05 mol %. In another aspect, provided herein is a method of treating a bacterial infection in a patient, comprising the step of administering a composition as described above.

In still another aspect, provided herein is a composition comprising a compound of formula (V), or a salt thereof, selected from the compounds of Table 2, or salts thereof, prepared according to a method described herein. Provided herein are particular embodiments of the composition (i)-(p), wherein:

(i) the compound of formula (V-1), or a salt thereof:

(V-1)

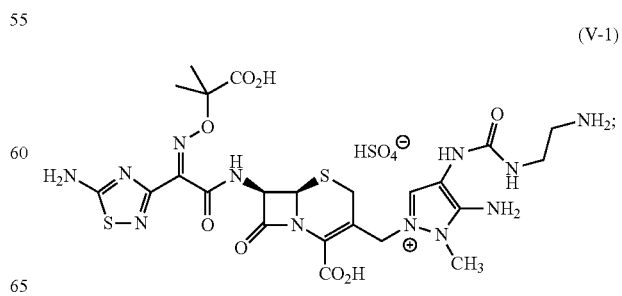

and
0.3-0.5% of one or more compound selected from:
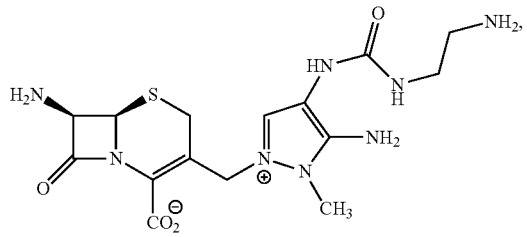
or a salt thereof; and
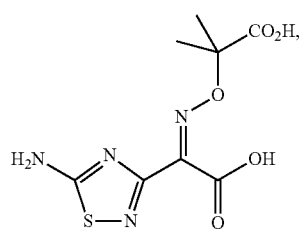 [SMILES: CC(C)(O/N=C(\C(=O)O)c1nsc(N)n1)C(=O)O]
or a salt thereof;
(j) the compound of formula (V-2), or a salt thereof:
(V-2)
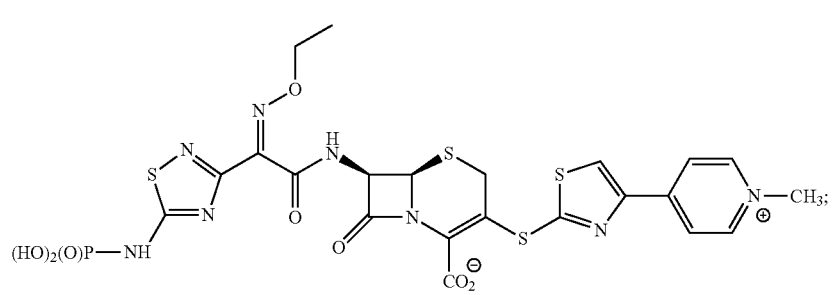
and
0.3-0.5% of one or more compound selected from:
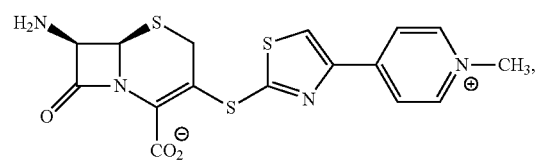
or a salt thereof; and
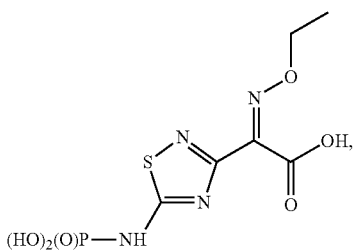
or a salt thereof;
(k) the compound of formula (V-3), or a salt thereof:
(V-3)
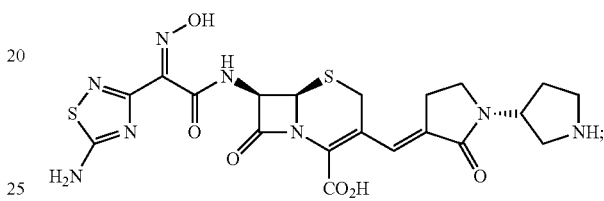
and
0.3-0.5% of one or more compound selected from:
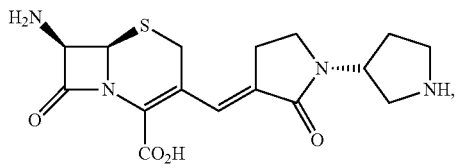
or a salt thereof; and
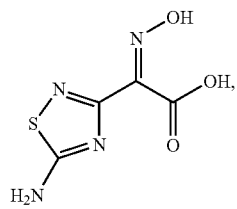 [SMILES: Nc1nc(/C(=N/O)C(=O)O)ns1]
or a salt thereof;

(I) the compound of formula (V-5), or a salt thereof:
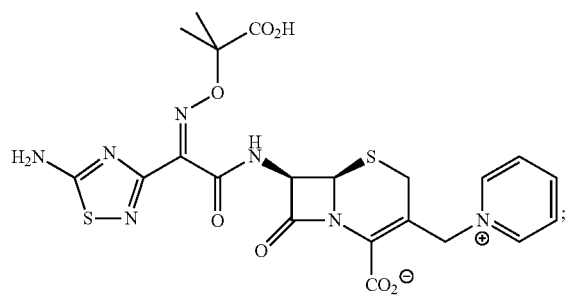
(V-5)
and
0.3-0.5% of one or more compound selected from:
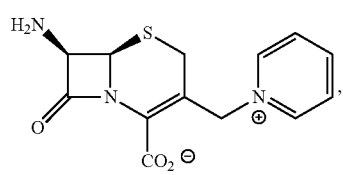
or a salt thereof; and
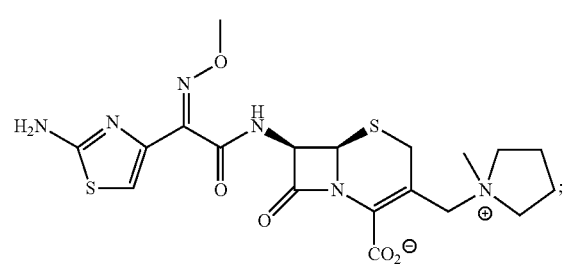
or a salt thereof;
(m) the compound of formula (V-6), or a salt thereof:
(V-6)
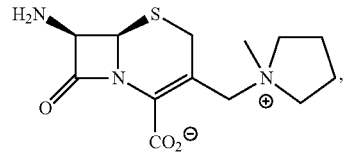
or a salt thereof; and
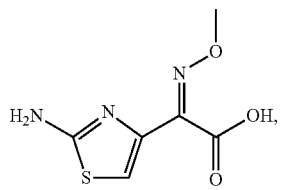
or a salt thereof;
(n) the compound of formula (V-9), or a salt thereof:
(V-9)
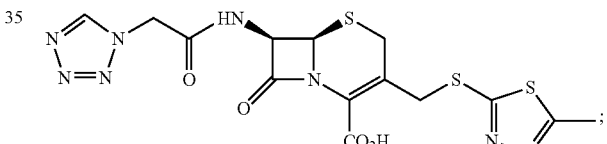
and
0.3-0.5% of one or more compound selected from:
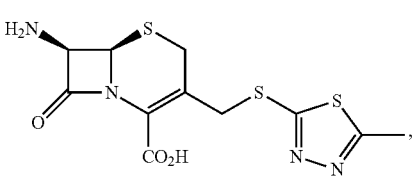 [SMILES: Cc1nnc(SCC2=C(C(=O)O)N3C(=O)[C@@H](N)[C@H]3SC2)s1]
or a salt thereof; and
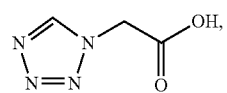
or a salt thereof;

(o) the compound of formula (V-26), or a salt thereof:

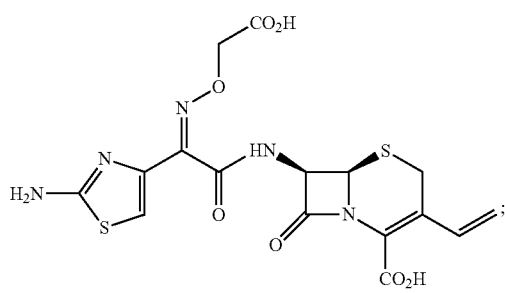

(V-26)

and
0.3-0.5% of one or more compound selected from:

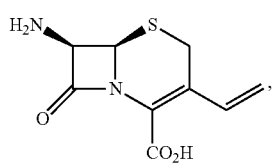

or a salt thereof; and

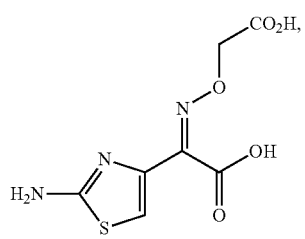 [SMILES: Nc1nc(/C(=N/OCC(=O)O)C(=O)O)cs1]

or a salt thereof; and (p) the compound of formula (V-16), or a salt thereof:

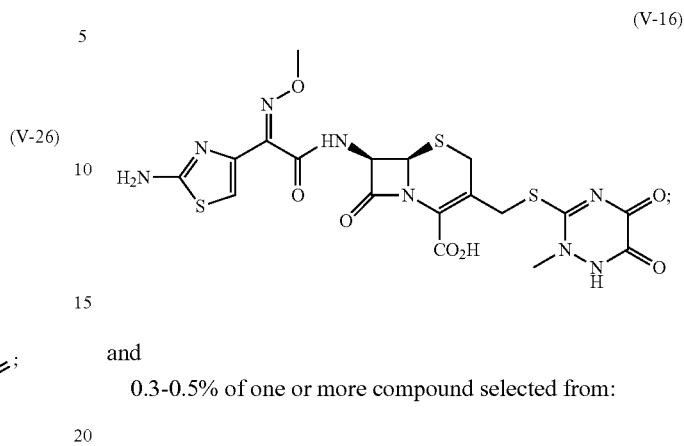

(V-16)

and
0.3-0.5% of one or more compound selected from:

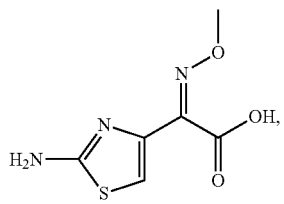

or a salt thereof; and

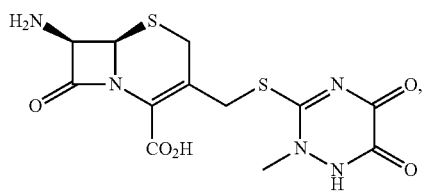 [SMILES: Cn1[nH]c(=O)c(=O)nc1SCC1=C(C(=O)O)N2C(=O)[C@@H](N)[C@H]2SC1]

or a salt thereof.

Uses and Methods of Treatment

In another aspect, provided herein is a method of treating a bacterial infection in a patient, comprising the step of administering to the patient a composition of embodiments (i)-(p). In another aspect, provided herein is a composition of embodiments (i)-(p) for use in the treatment of a bacterial infection in a patient. In another aspect, provided herein is the use of a composition of embodiments (i)-(p) for the manufacture of a medicament for the treatment of a bacterial infection in a patient.

In another aspect, provided herein is a composition comprising two or more compounds selected from the group consisting of:

(a) the compound of formula (II-1), or a salt thereof

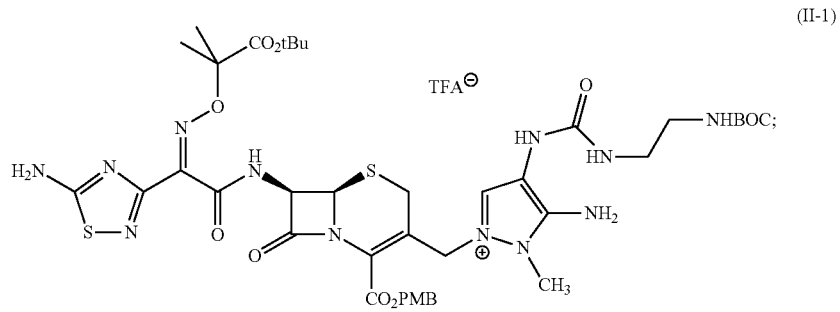

(b) the compound of formula (III-1), or a salt thereof

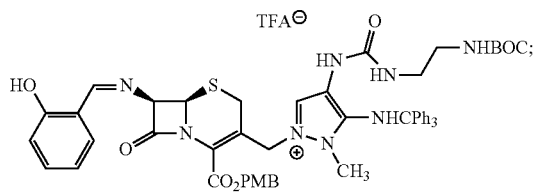

(c) the compound of formula (IIIc), or a salt thereof

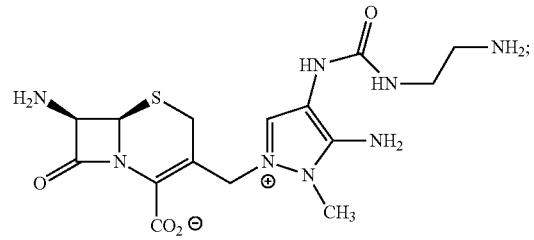

(d) the compound of formula (IV-1), or a salt thereof

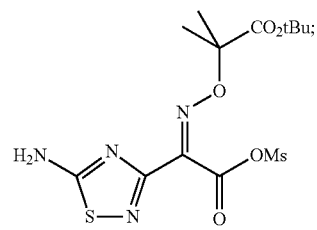

and (e) the compound of formula (IVb), or a salt thereof

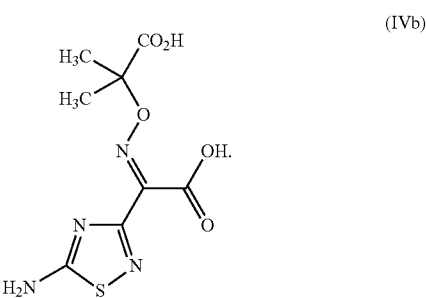 [SMILES: CC(C)(O/N=C(\C(=O)O)c1nsc(N)n1)C(=O)O]

In one embodiment, the composition further comprises the compound having the structure:

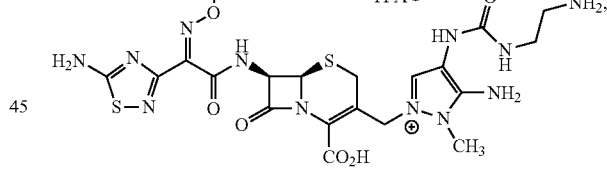

or a salt thereof.

Compounds of the Invention

Provided herein is a compound having the structure:

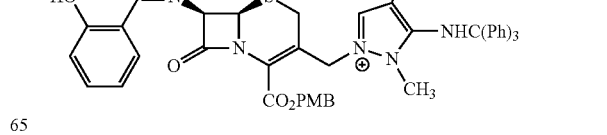

wherein $A^{\ominus}$ is an anion.

Also provided herein is a compound having the structure:

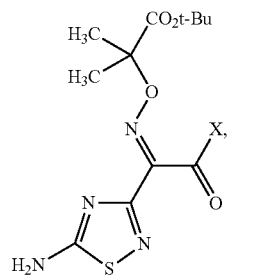

wherein X is selected from the group consisting of halogen, —OC(O)R$_8$ and —OSO$_2$R$_8$, wherein R$_8$ is selected from the group consisting of alkyl, heteroalkyl, aryl and heteroaryl.

Particular embodiments of the compounds of formulas (II), (III) and (IV) are listed in Table 1. For example, in the synthesis of the antibiotic compound ceftolozane, the compounds of formulas (II), (III) and (IV) can have the structures of formulas (II-1), (III-1) and (IV-1), respectively.

In one embodiment, the compound of formula (IV-1) is prepared from the compound of formula (IVa):

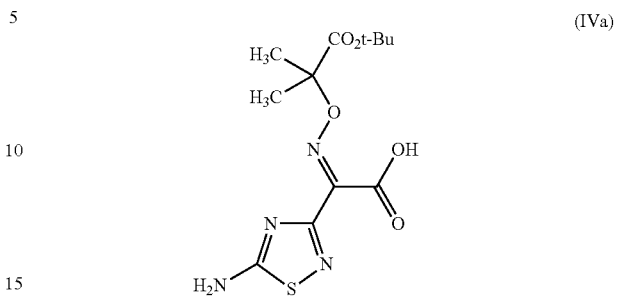

by a process comprising the steps of: (a) forming a mixture comprising potassium carbonate and the compound of formula (IVa); and (b) adding methasulfonyl chloride to the mixture of step (a) such that the compound of formula (IV-1) is formed.

(II-1)

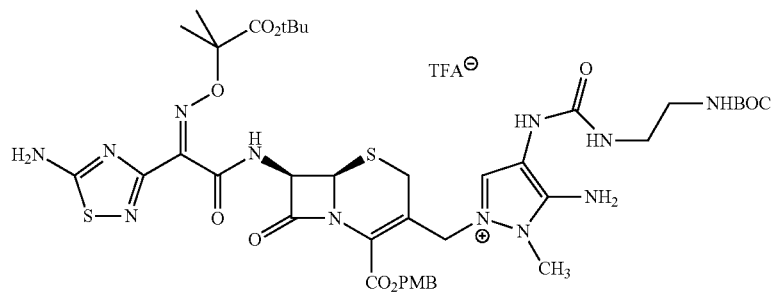

(III-1)

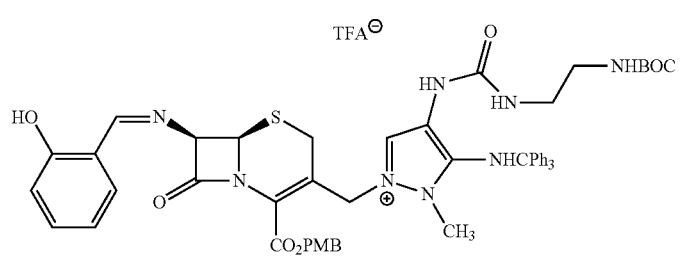

(IV-1)

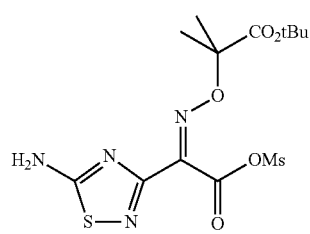

Synthesis

In one embodiment of the method, the suitable conditions comprise reacting in a mixture comprising an organic solvent and water. Organic solvents can be selected from the group consisting of aromatic solvents, aliphatic solvents, halogenated solvents, halogenated aromatic solvents, halogenated aliphatic solvents, ethers, halogenated ethers, esters and amides. In a particular embodiment, the organic solvent is selected from halogenated solvents. In another particular embodiment, the organic solvent is dichloromethane.

In another embodiment of the method, the suitable conditions comprise reacting in a mixture comprising an organic solvent and about 6-9 percent (w/w) water relative to the compound of formula (III), or salt thereof. In a particular embodiment, the suitable conditions comprise reaction in a mixture comprising an organic solvent and about 6-8 percent (w/w) water relative to the compound of formula (III), or salt thereof. In still another embodiment, the suitable conditions comprise reacting in a mixture comprising dichloromethane and about 6-9 percent of water relative to the compound of formula (III), or salt thereof.

Figure 11:
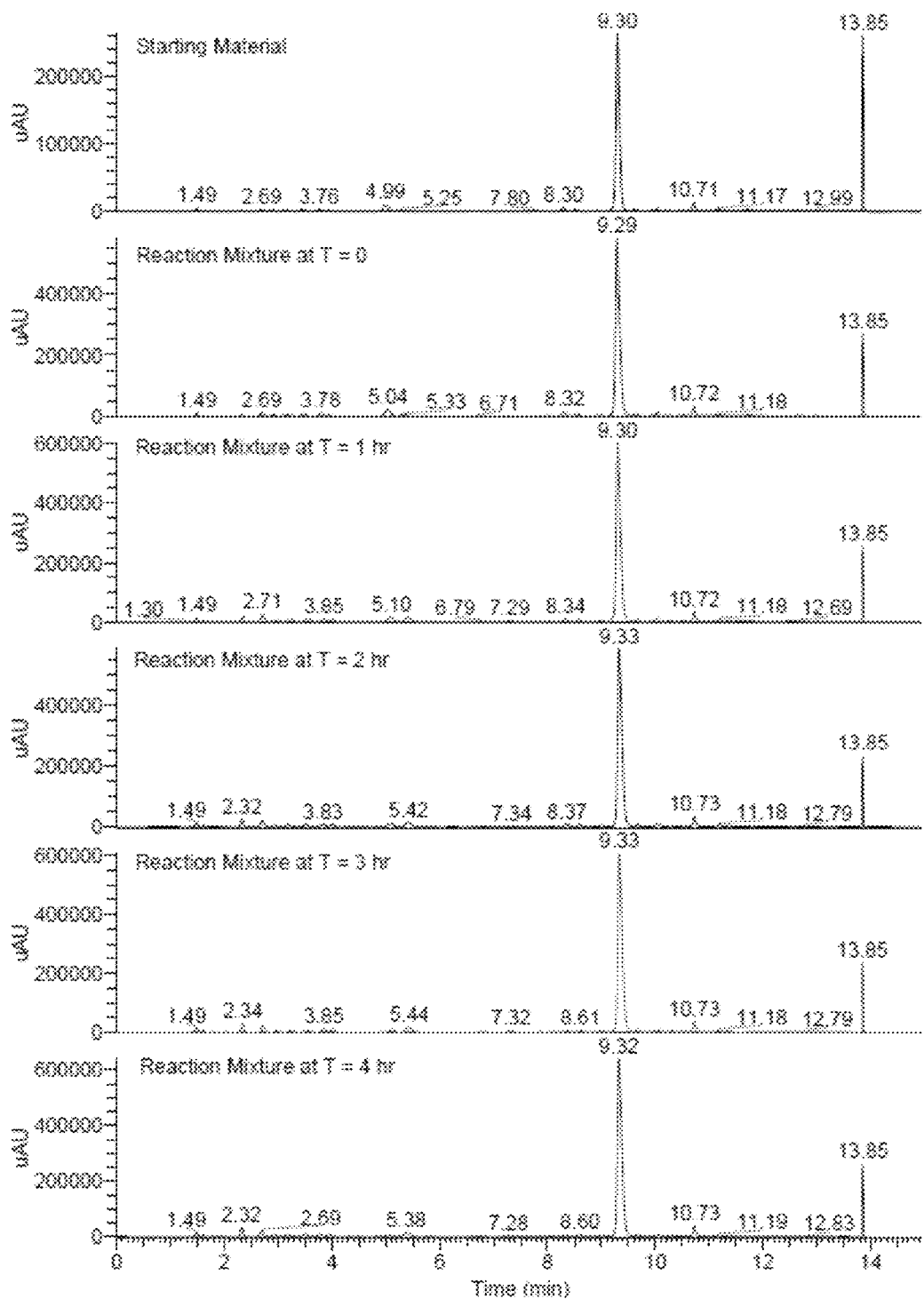
FIG. 11 depicts the HPLC chromatograms of Example 2.

Notably, the compound of formula (III) is hydrolytically stable under the reaction conditions, in the absence of the compound of formula (IV). As shown in FIG. 11 and described in Example 2, compound (III-1) was combined with dichloromethane and water in the same relative amounts as in Example 1. Upon stirring for four hours, no hydrolysis of (III-1) was observed. In contrast, under the same solvent, temperature and time conditions, but in the presence of compound (IV-1), compound (III-1) reacts to form compound (III-1).

In some embodiments, the method further comprises the step of reacting the compound of formula (II), or a salt thereof, under suitable conditions to form a compound of formula (V), or a salt thereof, wherein the compound of formula (V) is selected from the compounds of Table 2, or salts thereof. In some embodiments, the suitable conditions comprise reacting the compound of formula (II) with strong acid. In a particular embodiment, the strong acid is trifluoroacetic acid.

DEFINITIONS

Pharmaceutically acceptable salts are known to those of skill in the art. In some of the embodiments described herein, the compounds of formulas (II) and (III) are trifluoroacetate salts.

Oxygen and nitrogen protecting groups are known to those of skill in the art. Oxygen protecting groups include, but are not limited to methyl ethers, substituted methyl ethers (e.g., MOM (methoxymethyl ether), MTM (methylthiomethyl ether), BOM (benzyloxymethyl ether), PMBM or MPM (p-methoxybenzyloxymethyl ether), to name a few), substituted ethyl ethers, substituted benzyl ethers, silyl ethers (e.g., TMS (trimethylsilyl ether), TES (triethylsilylether), TIPS (triisopropylsilyl ether), TBDMS (t-butyldimethylsilyl ether), tribenzyl silyl ether, TBDPS (t-butyldiphenyl silyl ether), to name a few), esters (e.g., formate, acetate, benzoate (Bz), trifluoroacetate, dichloroacetate, to name a few), carbonates, cyclic acetals and ketals. Nitrogen protecting groups include, but are not limited to, carbamates (including methyl, ethyl and substituted ethyl carbamates (e.g., Troc), to name a few) amides, cyclic imide derivatives, N-alkyl and N-aryl amines, benzyl amines, substituted benzyl amines, trityl amines, imine derivatives, and enamine derivatives, for example.

Exemplary anions include, but are not limited to, carboxylates (e.g., acetate, benzoate, trifluoroacetate), halides (e.g., chloride, bromide, iodide), sulfate (e.g., monosulfate, bisulfate) and phosphate (e.g., monophosphate).

In some embodiments, alkyl groups and groups comprising an alkyl group (e.g., alkoxy, alkanoyl, alkylamino, aminoalkyl, heteroalkyl) comprise 1-6 carbon atoms. In some embodiments, aryl groups and groups comprising aryl groups (e.g., aroyl) comprise 6-12 carbon atoms. In some embodiments, heteroaryl groups and groups comprising heteroaryl groups (e.g., heteroaroyl) comprise 1-10 carbon atoms and 1-4 heteroatoms selected from oxygen, nitrogen and sulfur.

TABLE 1

US 9,006,421 B2
TABLE 1-continued
| | Formula (II) | Formula (III) | Formula (IV) |
|---|---|---|---|
| 5 | 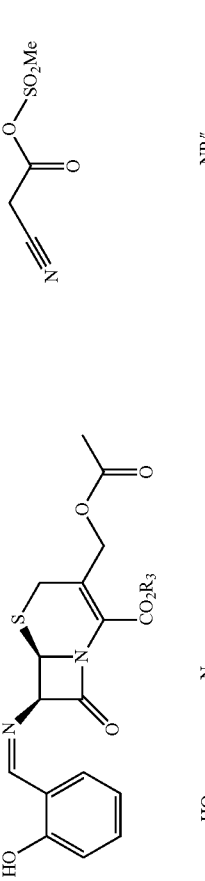 | 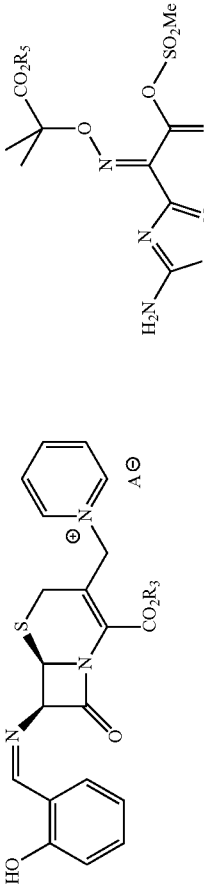 | 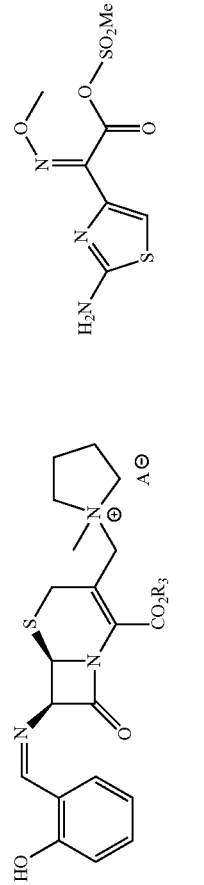 |
| 6 | 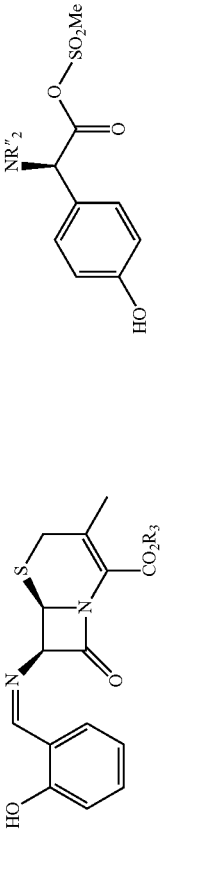 | | |
| 7 | 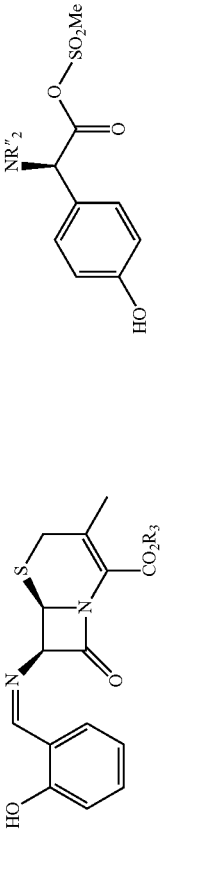 | 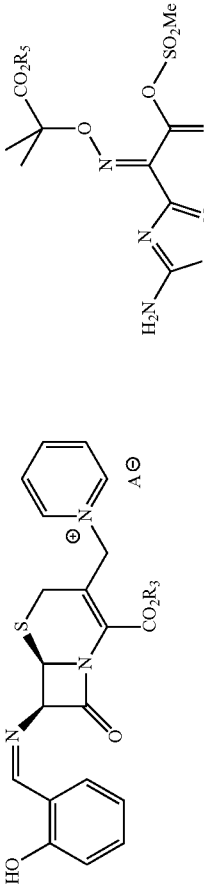 | |
| 8 | 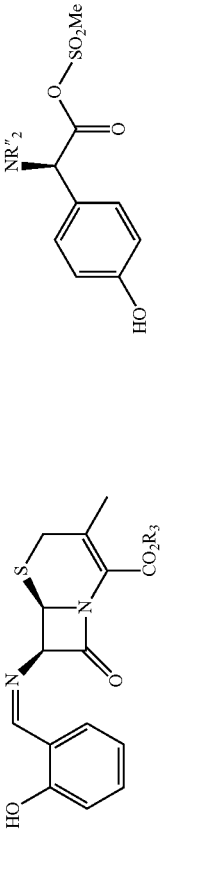 | 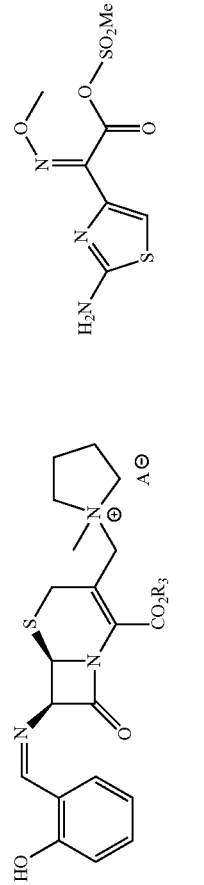 | |

TABLE 1-continued

| | Formula (II) | Formula (III) | Formula (IV) |
|---|---|---|---|
| 9 | | | |
| 10 | | | |
| 11 | | | |
| 12 | | | |
| 13 | | | |

TABLE 1-continued

| | Formula (II) | Formula (III) | Formula (IV) |
|---|---|---|---|
| 14 | | | |
| 15 | | | |
| 16 | | | |
| 17 | | | |

TABLE 1-continued

TABLE 1-continued

| | Formula (II) | Formula (III) | Formula (IV) |
|---|---|---|---|
| 22 | | | |
| 23 | | | |
| 24 | | | |

TABLE 1-continued

| | Formula (II) | Formula (III) | Formula (IV) |
|---|---|---|---|
| 25 | | | |
| 26 | | | |
| 27 | | | |

TABLE 1-continued

| | Formula (II) | Formula (III) | Formula (IV) |
|---|---|---|---|
| 28 | | | |
| 29 | | | |
| 30 | | | |

TABLE 1-continued

TABLE 2
Formula (V)
V-1
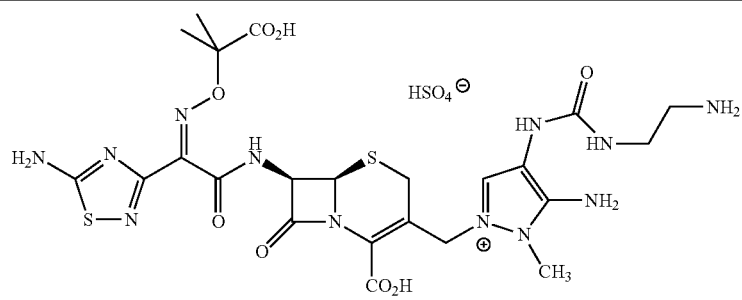
V-2
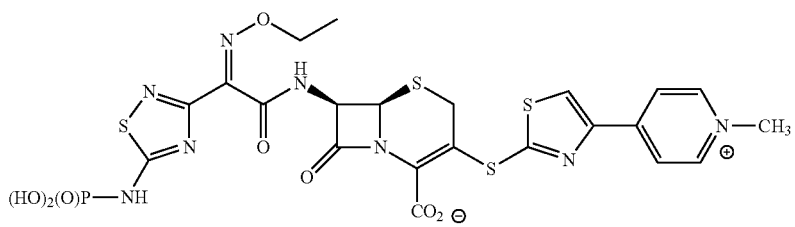
V-3
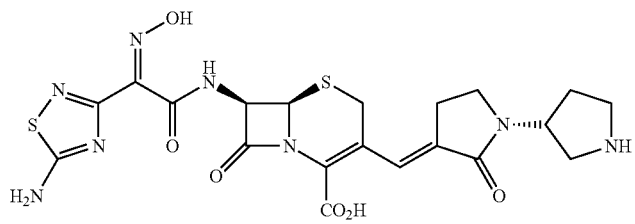
V-4
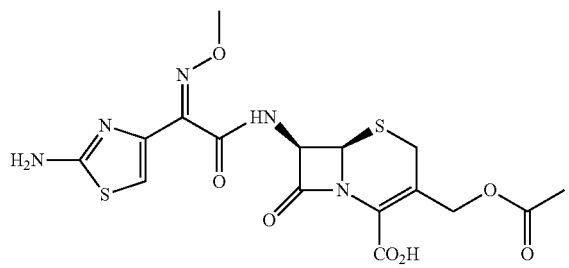 [SMILES: CO/N=C(\C(=O)N[C@@H]1C(=O)N2C(C(=O)O)=C(COC(C)=O)CS[C@H]12)c1csc(N)n1]
V-5
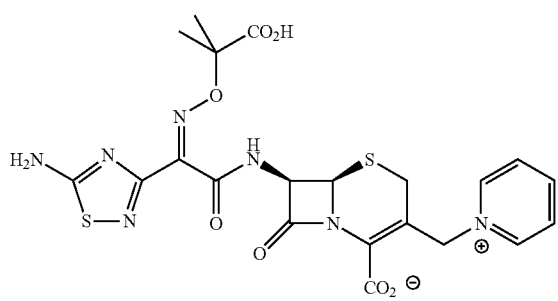
V-6
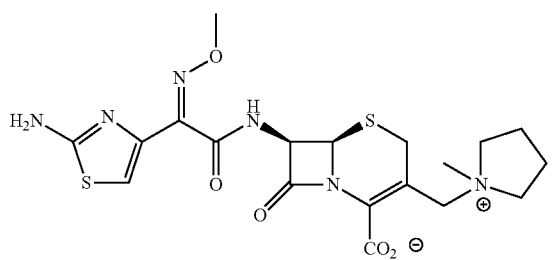

TABLE 2-continued
Formula (V)
| | |
|---|---|
| V-7 | 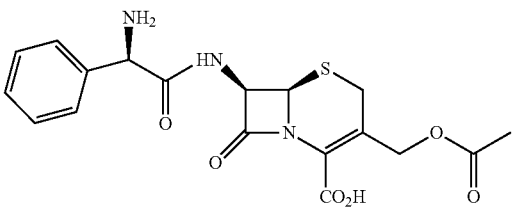 [SMILES: CC(=O)OCC1=C(C(=O)O)N2C(=O)[C@@H](NC(=O)[C@H](N)c3ccccc3)[C@H]2SC1] |
| V-8 | 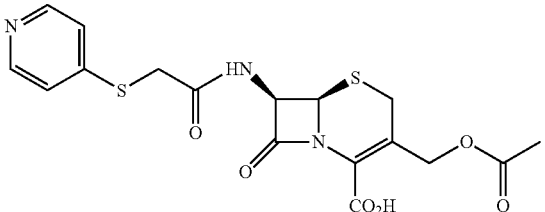 |
| V-9 | 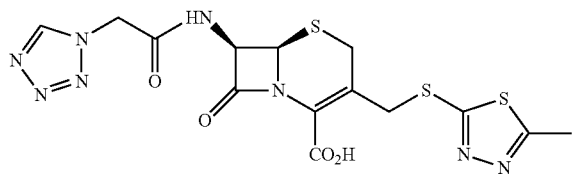 [SMILES: Cc1nnc(SCC2=C(C(=O)O)N3C(=O)[C@@H](NC(=O)Cn4cnnn4)[C@H]3SC2)s1] |
| V-10 | 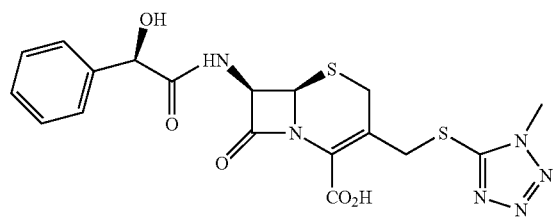 [SMILES: Cn1nnnc1SCC1=C(C(=O)O)N2C(=O)[C@@H](NC(=O)[C@H](O)c3ccccc3)[C@H]2SC1] |
| V-11 | 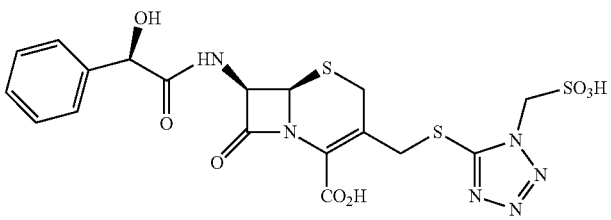 [SMILES: O=C(O)C1=C(CSc2nnnn2CS(=O)(=O)O)CS[C@@H]2[C@H](NC(=O)[C@H](O)c3ccccc3)C(=O)N12] |
| V-12 | 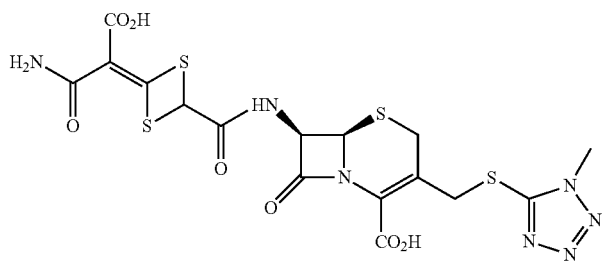 [SMILES: Cn1nnnc1SCC1=C(C(=O)O)N2C(=O)[C@@H](NC(=O)C3SC(=C(C(N)=O)C(=O)O)S3)[C@H]2SC1] |
| V-13 | 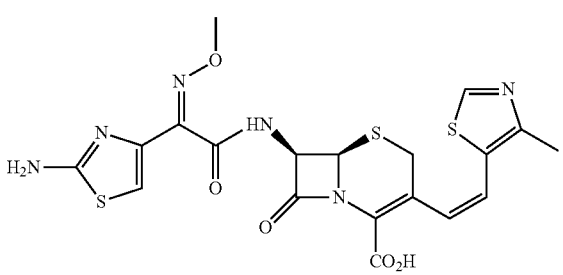 [SMILES: CO/N=C(\C(=O)N[C@@H]1C(=O)N2C(C(=O)O)=C(/C=C\c3scnc3C)CS[C@H]12)c1csc(N)n1] |

TABLE 2-continued
Formula (V)
V-14
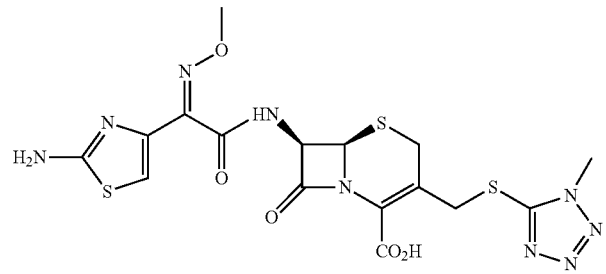 [SMILES: CO/N=C(\C(=O)N[C@@H]1C(=O)N2C(C(=O)O)=C(CSc3nnnn3C)CS[C@H]12)c1csc(N)n1]
V-15
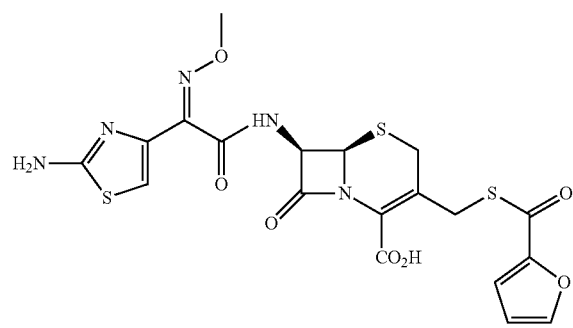 [SMILES: CO/N=C(\C(=O)N[C@@H]1C(=O)N2C(C(=O)O)=C(CSC(=O)c3ccco3)CS[C@H]12)c1csc(N)n1]
V-16
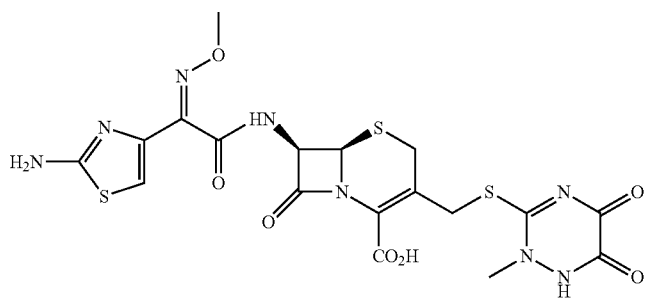 [SMILES: CO/N=C(\C(=O)N[C@@H]1C(=O)N2C(C(=O)O)=C(CSc3nc(=O)c(=O)[nH]n3C)CS[C@H]12)c1csc(N)n1]
V-17
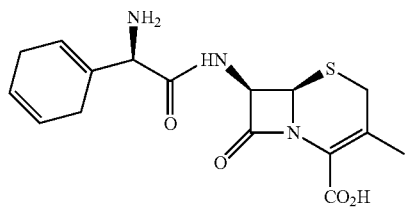 [SMILES: CC1=C(C(=O)O)N2C(=O)[C@@H](NC(=O)[C@H](N)C3=CCC=CC3)[C@H]2SC1]
V-18
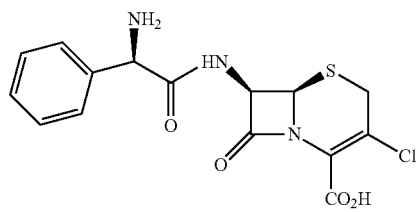 [SMILES: N[C@@H](C(=O)N[C@@H]1C(=O)N2C(C(=O)O)=C(Cl)CS[C@H]12)c1ccccc1]
V-19
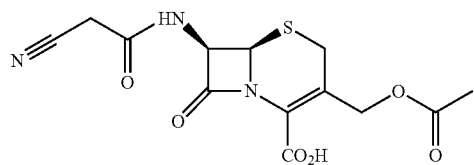 [SMILES: CC(=O)OCC1=C(C(=O)O)N2C(=O)[C@@H](NC(=O)CC#N)[C@H]2SC1]

TABLE 2-continued

Formula (V)

V-20

V-21

V-22

V-23

V-24

V-25

TABLE 2-continued
Formula (V)
V-26 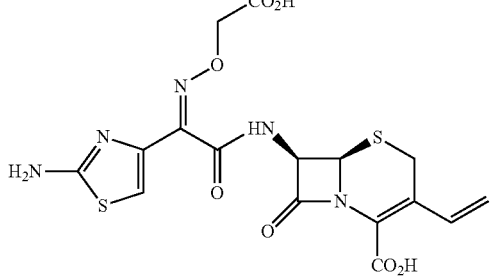
V-27 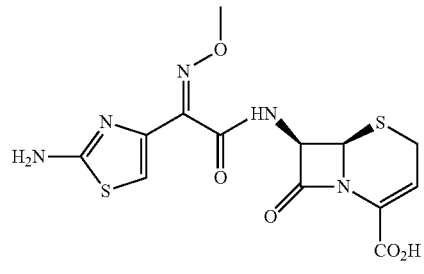 [SMILES: CO/N=C(\C(=O)N[C@@H]1C(=O)N2C(C(=O)O)=CCS[C@H]12)c1csc(N)n1]
V-28 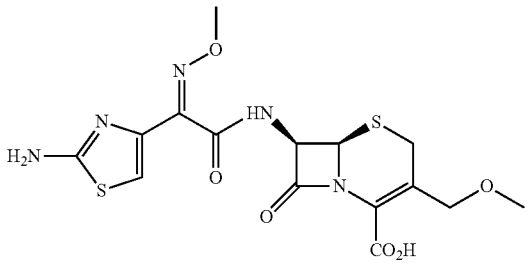 [SMILES: COCC1=C(C(=O)O)N2C(=O)[C@@H](NC(=O)/C(=N\OC)c3csc(N)n3)[C@H]2SC1]
V-29 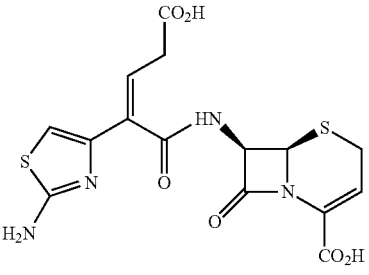 [SMILES: Nc1nc(/C(=C/CC(=O)O)C(=O)N[C@@H]2C(=O)N3C(C(=O)O)=CCS[C@H]23)cs1]
V-30 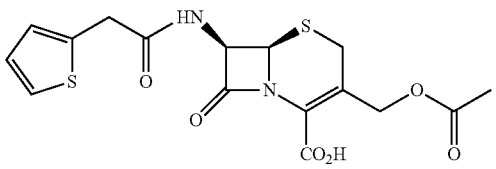 [SMILES: CC(=O)OCC1=C(C(=O)O)N2C(=O)[C@@H](NC(=O)Cc3cccs3)[C@H]2SC1]

TABLE 2-continued

Formula (V)

V-31

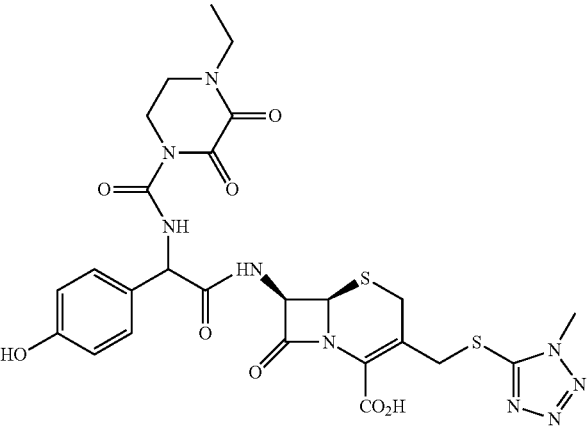 [SMILES: CCN1CCN(C(=O)NC(C(=O)N[C@@H]2C(=O)N3C(C(=O)O)=C(CSc4nnnn4C)CS[C@H]23)c2ccc(O)cc2)C(=O)C1=O]

V-32

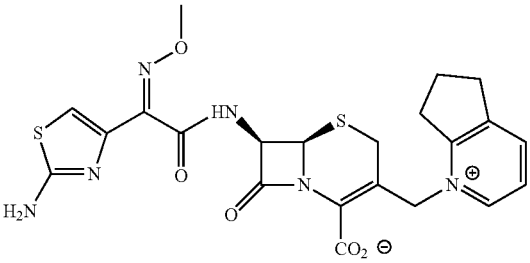

EXAMPLES

Materials and Instrumentation

Compound characterization was obtained by high resolution mass spectrometry (HRMS) and high resolution mass spectrometry/mass spectrometry (HR MS/MS). Samples were dissolved in solution and the sample solutions were directly infused into time-of-flight (TOF) mass spectrometer to obtain parent (MS) and product scans (MS/MS) of analyte. Suitable materials and instrumentation are known to persons of skill in the art.

Example 1

Synthesis of Compound (V-1)

(1) Synthesis of Compound (IV-1)

(Z)-2-(5-amino-1,2,4-thiadiazol-3-yl)-2-(((1-(tert-butoxy)-2-methyl-1-oxopropan-2-yl)oxy)imino)acetic methanesulfonic anhydride

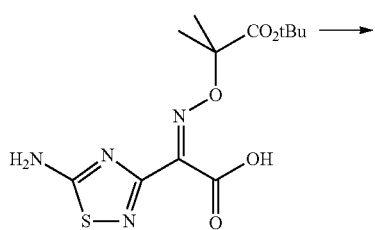

⟶

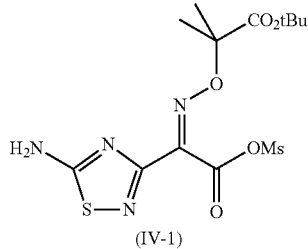

(IV-1)

A 5.0 liter reactor was charged with N,N-dimethylacetamide (1.4 L). Solid (Z)-2-(5-amino-1,2,4-thiadiazol-3-yl)-2-(((1-(tert-butoxy)-2-methyl-1-oxopropan-2-yl)oxy)imino) acetic acid (250 g, 1 eq., prepared according to the method disclosed in U.S. Pat. No. 7,129,232) was added to the reactor at ambient temperature and the mixture was stirred until the solid was dissolved. The solution was cooled to about 4° C. (target: 2-5° C.) and stirred for another 10-15 minutes. Potassium carbonate (106.7 g, 184.9 mmol, 1.1 eq.) was added to the reactor in one portion. Methanesulfonyl chloride (118.0 mL, 2.2 eq.) was added to the reactor at a rate of about 5 mL/min while maintaining the batch temperature <10° C. The reaction was stirred for 1-2 hours at about 6° C., then cooled to about 0-5° C. Ethyl acetate (2.5 L, 10 volumes) was added to the reactor while maintaining a temperature of about 0-5° C. 1.6% HCl (aq) (1.35 L) was added to the reactor, maintaining a temperature of about 10-15° C. The biphasic mixture was agitated and the layers were then separated. The organic layer was washed with sodium chloride solution, dried with sodium sulfate and concentrated under reduced pressure to obtain crude material. The crude material was dissolved in ethyl acetate (150 mL) and filtered over silica gel.

The filtrate was concentrated under reduced pressure to yield the title compound (299 g, 96.7%) as a colorless solid. Exact Mass: 408.08. HRMS: 409.0846 (M+1).

(2) Synthesis of Compound (III-1)

5-amino-4-(3-(2-((tert-butoxycarbonyl)amino)ethyl) ureido)-2-(((6R,7R)-7-((Z)-(2-hydroxybenzylidene) amino)-2-(((4-methoxybenzyl)oxy)carbonyl)-8-oxo-5-thia-1-azabicyclo[4.2.0]oct-2-en-3-yl)methyl)-1-methyl-1H-pyrazol-2-ium trifluoroacetate

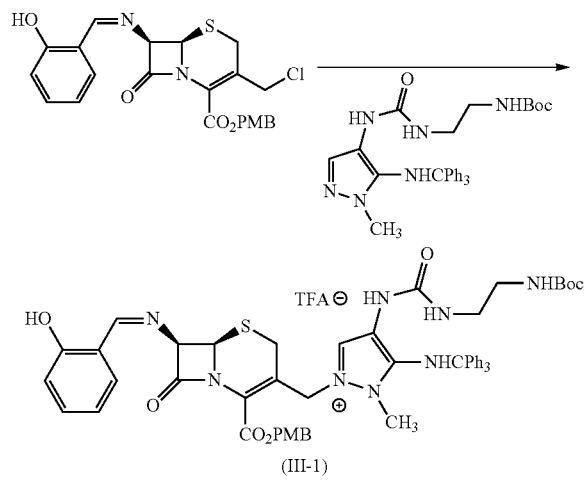

(III-1)

Compound (III-1) was prepared by coupling the compound (6R,7R)-4-methoxybenzyl 3-(chloromethyl)-7-((Z)-(2-hydroxybenzylidene)amino)-8-oxo-5-thia-1-azabicyclo[4.2.0]oct-2-ene-2-carboxylate (purchased from Nippon Chemicals, Japan) with the compound tert-butyl (2-(3-(1-methyl-5-(tritylamino)-1H-pyrazol-4-yl)ureido)ethyl)carbamate (UBT, prepared according to the method disclosed in U.S. Pat. No. 7,129,232).

In a reactor, UBT (274 g) was dissolved in 1 L of N-methylpyrrolidone (NMP) at 35-45° C. The solution was cooled to 15-20° C. SCLE (200 g) was added to the solution and stirred until it was completely dissolved. Then added 104 mL of N,O-Bis(trimethylsilyl)acetamide (BSA) dropwise in 30 minutes, followed by addition of 98.2 g potassium iodide (KI) in 6-8 portions, and maintained the temperature between 20-25° C. The resulting mixture was stirred at 15-25° C. for about 45-50 hours. The forgoing solution was then slowly added to 5% sodium trifluoro acetate (4 L) at room temperature in 3 hours and precipitates were formed. The slurry was filtered and washed with 2 L deionized water for 4 times, and 4 L of heptanes for 3 times. The wet cake was dried under nitrogen with vacuum until it reached a constant weight. The resulting compound (III-1) was isolated as a light yellow solid (569 g, 86.5%). Exact Mass (-TFA):977.40. HRMS:977.4025 (M+).

(3) Synthesis of Compound (II-1)

5-amino-2-(((6R,7R)-7-((Z)-2-(5-amino-1,2,4-thiadiazol-3-yl)-2-(((1-(tert-butoxy)-2-methyl-1-oxopropan-2-yl)oxy)imino)acetamido)-2-(((4-methoxybenzyl)oxy)carbonyl)-8-oxo-5-thia-1-azabicyclo[4.2.0] oct-2-en-3-yl)methyl)-4-(3-(2-((tert-butoxycarbonyl) amino)ethyl)ureido)-1-methyl-1H-pyrazol-2-ium trifluoroacetate

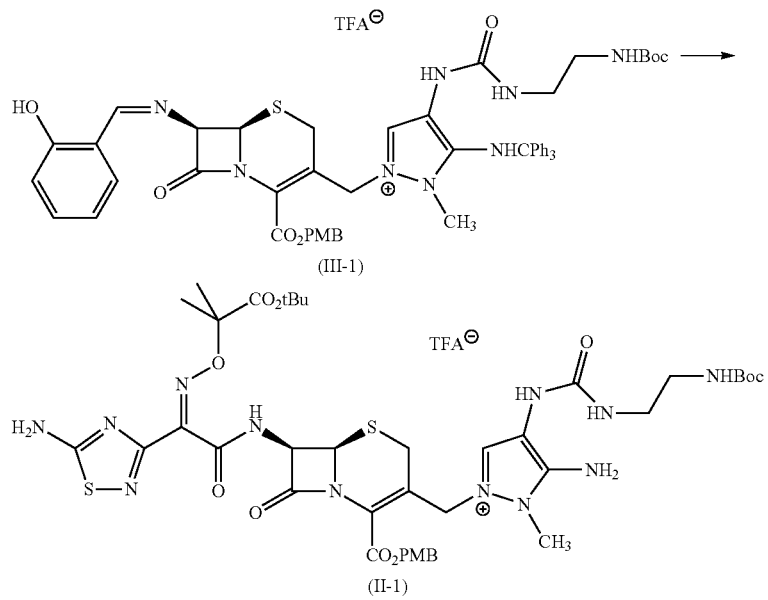

A reactor was charged with compound (III-1) (150 g), water (11.25 mL), compound (IV-1) (60 g), and dichloromethane (265 mL). The mixture was stirred for three hours at room temperature, then added to methyl tertiary butyl ether (1.5 L) over the course of 2-3 hours, resulting in the formation of a solid. The solid was filtered and the filter cake was washed with additional methyl tertiary butyl ether (1.0 L). The solid was dried under vacuum to yield the title compound (142.1 g, 81.2%). Exact Mass: 943.36 (-TFA). HRMS: 943.3555 (M+).

(4) Synthesis of Ceftolozane Trifluoroacetate

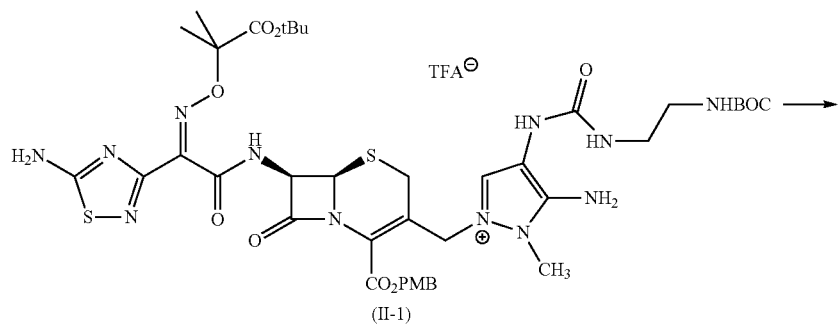

(II-1)

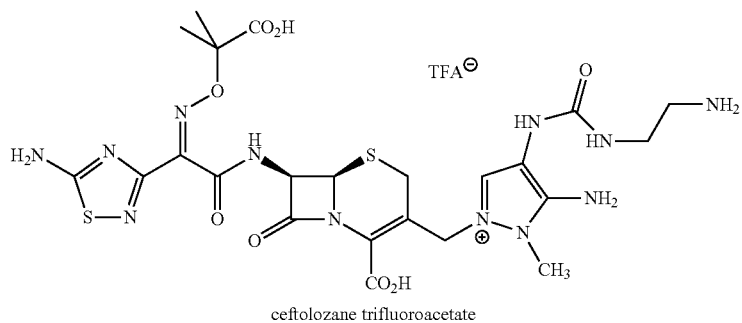

ceftolozane trifluoroacetate

Compound (II-1) was dissolved in dichloromethane. Trifluoroacetic acid and anisole were added and the reaction was stirred for about 3 hours. Methyl tertiary butyl ether was added, causing the formation of a precipitate. The precipitate was collected by filtration and dried under vacuum to yield the title compound. Exact Mass (-TFA): 667.18. HRMS: 667.1810 (M+).

(5) Synthesis of Compound (V-1)

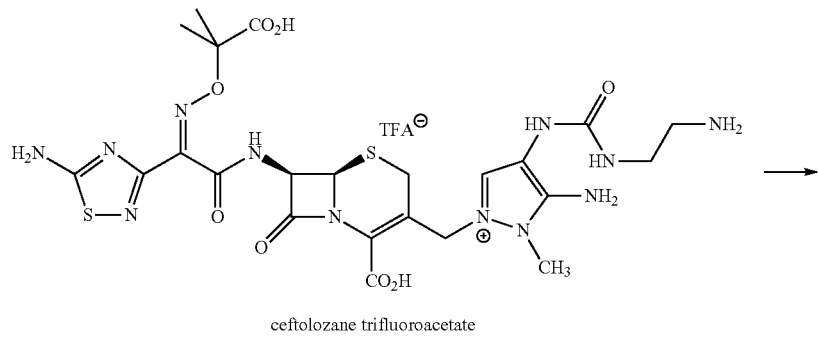

ceftolozane trifluoroacetate

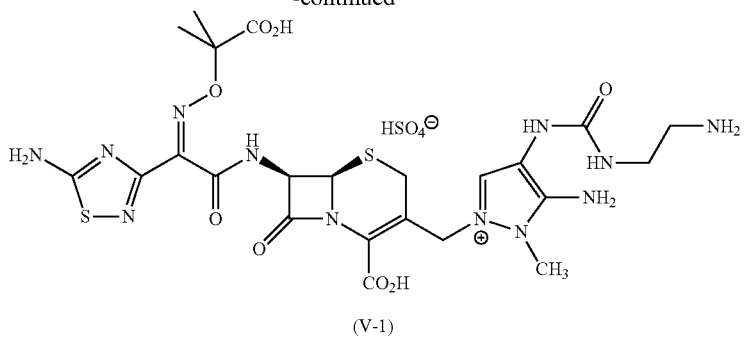

(V-1)

Ceftolozane trifluoroacetate (5 g) was dissolved in water (40 mL) and filtered. The solution was purified by HPLC using a Waters Sunfire C18 (50×100 mm, 5 µm) column with an eluent comprising Solvent A: acetonitrile+0.08% sulfuric acid (v/v) and Solvent B: water+0.08% sulfuric acid (v/v).

Example 2

Compound (III-1)

(2.12 g) was dissolved in dichloromethane (3.75 ml). Water (160 uL) was added and the mixture was stirred for four hours, with hourly monitoring by HPLC.

Example 3

Synthesis of (6R,7R)-7-((Z)-2-(ethoxyimino)-2-(5-(phosphonoamino)-1,2,4-thiadiazol-3-yl)acetamido)-3-((4-(1-methylpyridin-1-ium-4-yl)thiazol-2-yl)thio)-8-oxo-5-thia-1-azabicyclo[4.2.0]oct-2-ene-2-carboxylate A reactor is charged with 4-(2-(((7R)-7-((Z)-(2-hydroxybenzylidene)amino)-2-(((4-methoxybenzyl)oxy)carbonyl)-8-oxo-5-thia-1-azabicyclo[4.2.0]oct-2-en-3-yl)thio)thiazol-4-yl)-1-methylpyridin-1-ium trifluoroacetate (1 eq), water (6-9 weight % relative to the Schiff base), (Z)-2-(5-(phosphonoamino)-1,2,4-thiadiazol-3-yl)-2-(ethoxyimino)acetic methanesulfonic anhydride (2.5 eq) and dichloromethane (1.75 mL per gram of Schiff base). The mixture is stirred for three hours at room temperature, then added to methyl tertiary butyl ether over the course of 2-3 hours, resulting in the formation of a solid. The solid is filtered and the filter cake was washed with additional methyl tertiary butyl ether. The filtered solid is deprotected using conventional methods and dried under vacuum to yield the title compound.

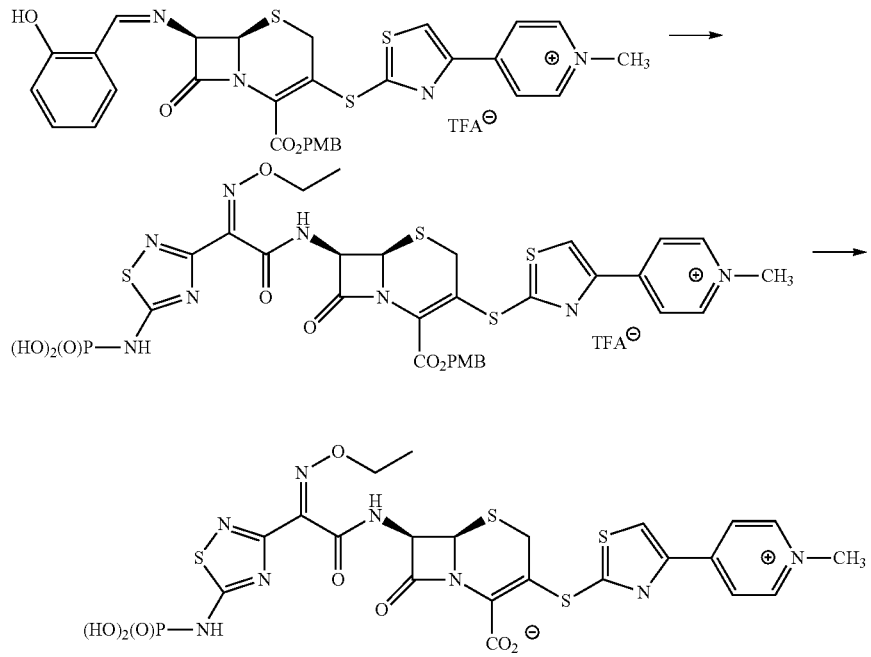

Example 4

Synthesis of (6R,7R)-7-((Z)-2-(5-amino-1,2,4-thiadiazol-3-yl)-2-(hydroxyimino)acetamido)-8-oxo-3-((E)-((R)-2-oxo-[1,3'-bipyrrolidin]-3-ylidene)methyl)-5-thia-1-azabicyclo[4.2.0]oct-2-ene-2-carboxylic acid

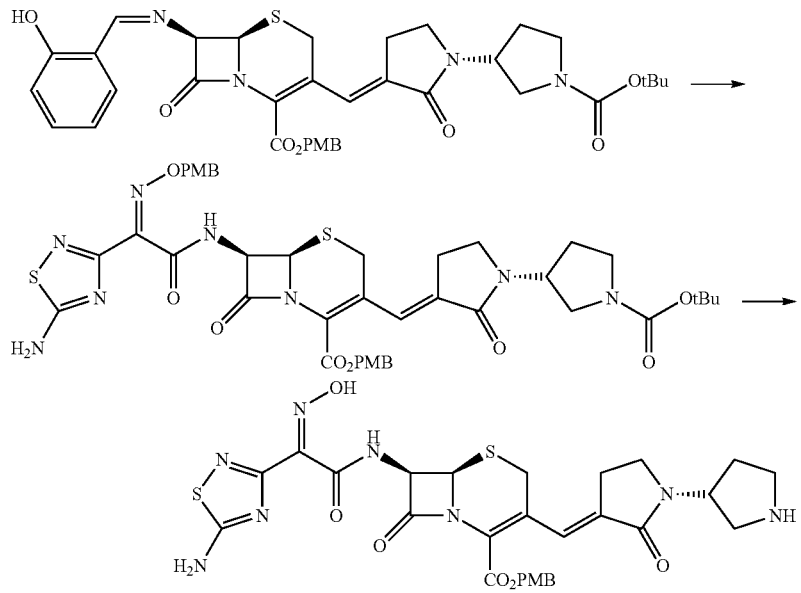

A reactor is charged with (7R)-4-methoxybenzyl-3-((E)-((R)-1'-(tert-butoxycarbonyl)-2-oxo-[1,3'-bipyrrolidin]-3-ylidene)methyl)-7-((Z)-(2-hydroxybenzylidene)amino)-8-oxo-5-thia-1-azabicyclo[4.2.0]oct-2-ene-2-carboxylate (1 eq), water (6-9 weight % relative to the Schiff base), (Z)-2-(5-amino-1,2,4-thiadiazol-3-yl)-2-(((4-methoxybenzyl)oxy)imino)acetic methanesulfonic anhydride (2.5 eq) and dichloromethane (1.75 mL per gram of Schiff base). The mixture is stirred for three hours at room temperature, then added to methyl tertiary butyl ether over the course of 2-3 hours, resulting in the formation of a solid. The solid is filtered and the filter cake was washed with additional methyl tertiary butyl ether. The filtered solid is deprotected using conventional methods and dried under vacuum to yield the title compound.

Example 5

Synthesis of (6R,7R)-7-((Z)-2-(5-amino-1,2,4-thiadiazol-3-yl)-2-(((2-carboxypropan-2-yl)oxy)imino)acetamido)-8-oxo-3-(pyridin-1-ium-1-ylmethyl)-5-thia-1-azabicyclo[4.2.0]oct-2-ene-2-carboxylate

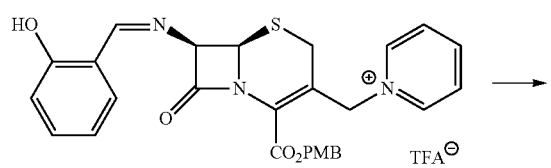

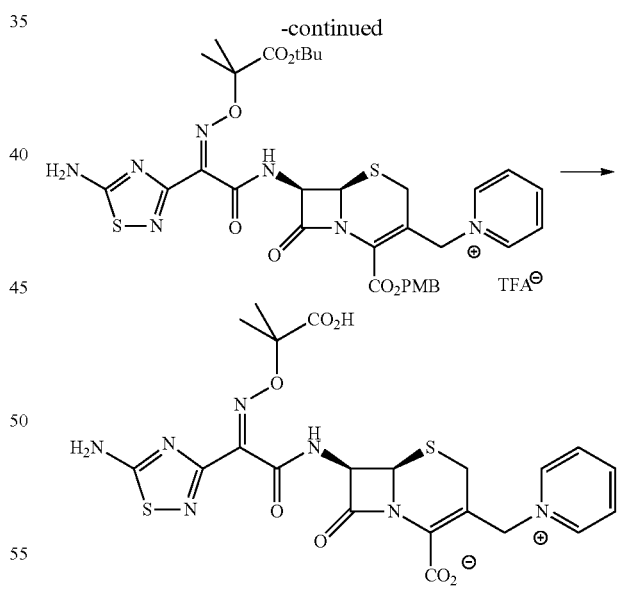

A reactor is charged with 1-(((7R)-7-((Z)-(2-hydroxybenzylidene)amino)-2-(((4-methoxybenzyl)oxy)carbonyl)-8-oxo-5-thia-1-azabicyclo[4.2.0]oct-2-en-3-yl)methyl)pyridin-1-ium trifluoroacetate (1 eq), water (6-9 weight % relative to the Schiff base), (Z)-2-(5-amino-1,2,4-thiadiazol-3-yl)-2-(((1-(tert-butoxy)-2-methyl-1-oxopropan-2-yl)oxy)imino)acetic methanesulfonic anhydride (2.5 eq) and dichloromethane (1.75 mL per gram of Schiff base). The mixture is stirred for three hours at room temperature, then added to methyl tertiary butyl ether over the course of 2-3 hours, resulting in the formation of a solid. The solid is filtered and the filter cake was washed with additional methyl tertiary butyl ether. The filtered solid is deprotected using conventional methods and dried under vacuum to yield the title compound.

Example 6

Synthesis of (6R,7R)-7-((Z)-2-(2-aminothiazol-4-yl)-2-(methoxyimino)acetamido)-3-((1-methylpyrrolidin-1-ium-1-yl)methyl)-8-oxo-5-thia-1-azabicyclo[4.2.0]oct-2-ene-2-carboxylate

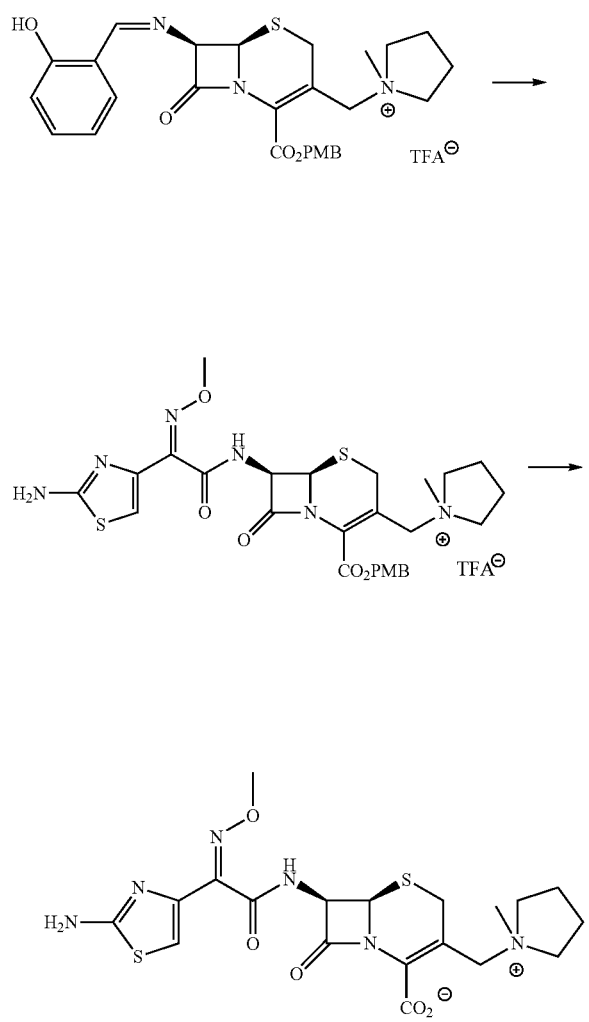

A reactor is charged with 1-(((6R,7R)-7-((Z)-(2-hydroxybenzylidene)amino)-2-(((4-methoxybenzyl)oxy)carbonyl)-8-oxo-5-thia-1-azabicyclo[4.2.0]oct-2-en-3-yl)methyl)-1-methylpyrrolidin-1-ium trifluoroacetate (1 eq), water (6-9 weight % relative to the Schiff base), (Z)-2-(2-aminothiazol-4-yl)-2-(methoxyimino)acetic methanesulfonic anhydride (2.5 eq) and dichloromethane (1.75 mL per gram of Schiff base). The mixture is stirred for three hours at room temperature, then added to methyl tertiary butyl ether over the course of 2-3 hours, resulting in the formation of a solid. The solid is filtered and the filter cake was washed with additional methyl tertiary butyl ether. The filtered solid is deprotected using conventional methods and dried under vacuum to yield the title compound.

Example 7

Synthesis of (6R,7R)-7-(2-(1H-tetrazol-1-yl)acetamido)-3-(((5-methyl-1,3,4-thiadiazol-2-yl)thio)methyl)-8-oxo-5-thia-1-azabicyclo[4.2.0]oct-2-ene-2-carboxylic acid

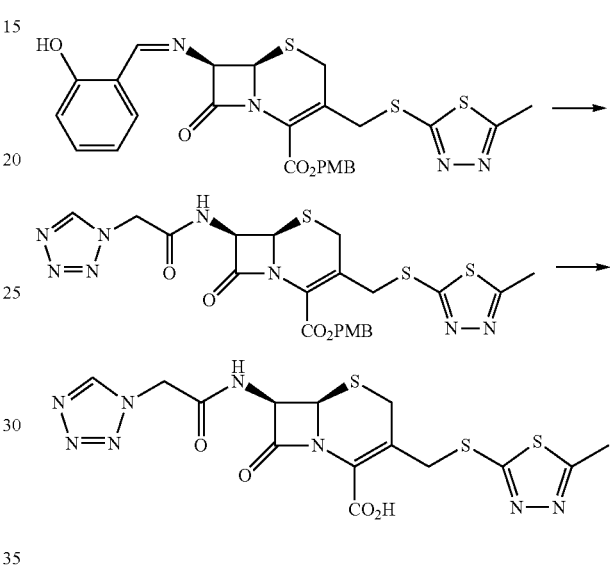

A reactor is charged with (6R,7R)-4-methoxybenzyl 7-((Z)-(2-hydroxybenzylidene)amino)-3-(((5-methyl-1,3,4-thiadiazol-2-yl)thio)methyl)-8-oxo-5-thia-1-azabicyclo[4.2.0]oct-2-ene-2-carboxylate (1 eq), water (6-9 weight % relative to the Schiff base), 2-(1H-tetrazol-1-yl)acetic methanesulfonic anhydride (2.5 eq) and dichloromethane (1.75 mL per gram of Schiff base). The mixture is stirred for three hours at room temperature, then added to methyl tertiary butyl ether over the course of 2-3 hours, resulting in the formation of a solid. The solid is filtered and the filter cake was washed with additional methyl tertiary butyl ether. The filtered solid is deprotected using conventional methods and dried under vacuum to yield the title compound.

Example 8

Synthesis of (6R,7R)-7-((Z)-2-(2-aminothiazol-4-yl)-2-((carboxymethoxy)imino)acetamido)-8-oxo-3-vinyl-5-thia-1-azabicyclo[4.2.0]oct-2-ene-2-carboxylic acid

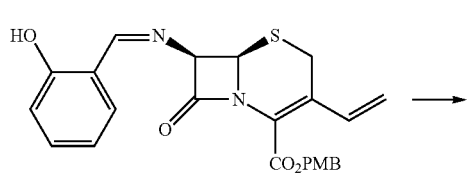

-continued

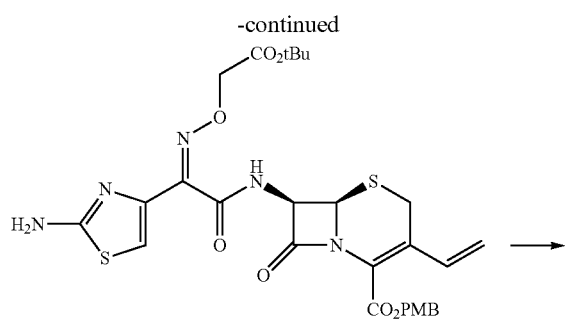

A reactor is charged with (6R,7R)-4-methoxybenzyl 7-((Z)-(2-hydroxybenzylidene)amino)-8-oxo-3-vinyl-5-thia-1-azabicyclo[4.2.0]oct-2-ene-2-carboxylate (1 eq), water (6-9 weight % relative to the Schiff base), (Z)-2-(2-aminothiazol-4-yl)-2-((2-(tert-butoxy)-2-oxoethoxy)imino) acetic methanesulfonic anhydride (2.5 eq) and dichloromethane (1.75 mL per gram of Schiff base). The mixture is stirred for three hours at room temperature, then added to methyl tertiary butyl ether over the course of 2-3 hours, resulting in the formation of a solid. The solid is filtered and the filter cake was washed with additional methyl tertiary butyl ether. The filtered solid is deprotected using conventional methods and dried under vacuum to yield the title compound.

Example 9

Synthesis of (6R,7R)-7-((Z)-2-(2-aminothiazol-4-yl)-2-(methoxyimino)acetamido)-3-(((2-methyl-5,6-dioxo-1,2,5,6-tetrahydro-1,2,4-triazin-3-yl)thio)methyl)-8-oxo-5-thia-1-aza bicyclo[4.2.0]oct-2-ene-2-carboxylic acid

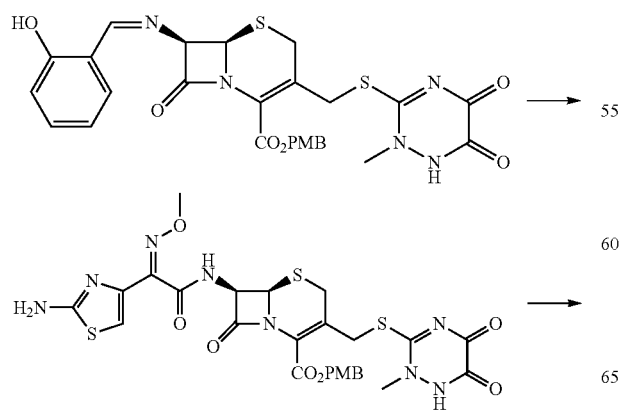

-continued

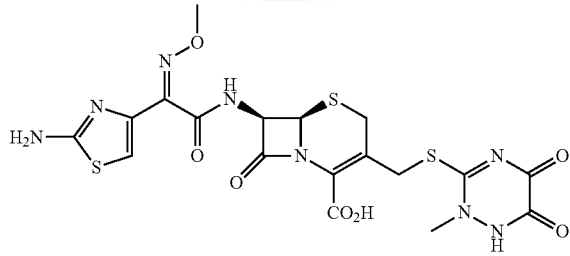

A reactor is charged with (6R,7R)-4-methoxybenzyl 7-((Z)-(2-hydroxybenzylidene)amino)-3-(((2-methyl-5,6-dioxo-1,2,5,6-tetrahydro-1,2,4-triazin-3-yl)thio)methyl)-8-oxo-5-thia-1-azabicyclo[4.2.0]oct-2-ene-2-carboxylate (1 eq), water (6-9 weight % relative to the Schiff base), (Z)-2-(2-aminothiazol-4-yl)-2-(methoxyimino)acetic methanesulfonic anhydride (2.5 eq) and dichloromethane (1.75 mL per gram of Schiff base). The mixture is stirred for three hours at room temperature, then added to methyl tertiary butyl ether over the course of 2-3 hours, resulting in the formation of a solid. The solid is filtered and the filter cake was washed with additional methyl tertiary butyl ether. The filtered solid is deprotected using conventional methods and dried under vacuum to yield the title compound.

What is claimed is:

1. A method for preparing a compound of formula (II), or a salt thereof,

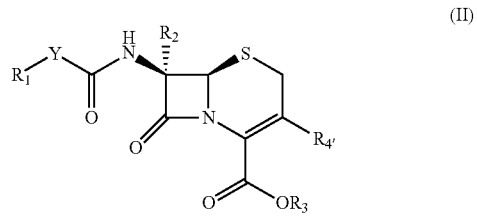

(II)

comprising the step of reacting a compound of formula (III), or a salt thereof,

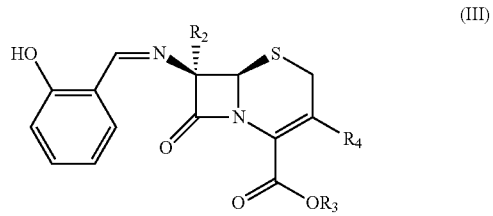

(III)

with a compound of formula (IV), or a salt thereof,

(IV)

in a mixture comprising an organic solvent and water, to form a compound of formula (II), or a salt thereof;

wherein:

R₁ is selected from the group consisting of:

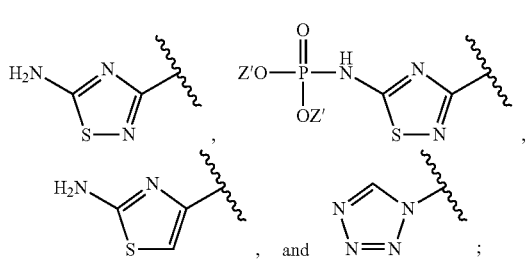

, and ;

wherein Z' is independently hydrogen or an oxygen protecting group;

Y is selected from the group consisting of:

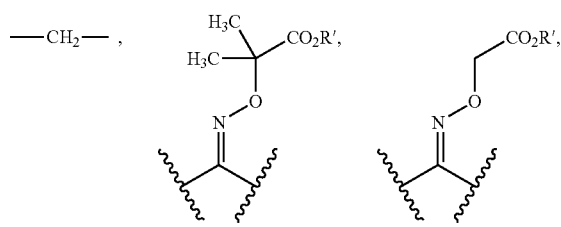

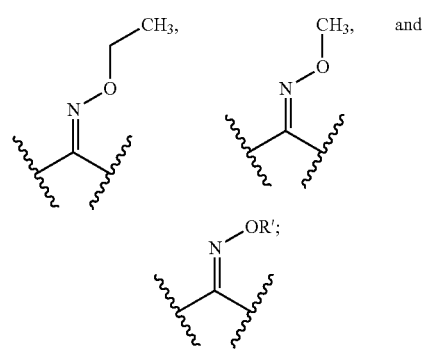

wherein R' is selected from the group consisting of hydrogen and an oxygen protecting group;

$R_2$ is hydrogen;

$R_3$ is selected from the group consisting of hydrogen and an oxygen protecting group; and $R_4$ and $R_{4'}$ are each independently selected from the group consisting of:

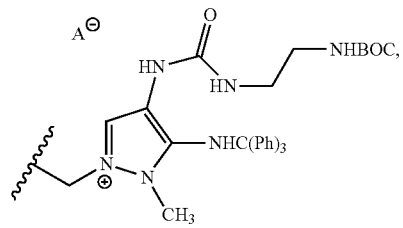

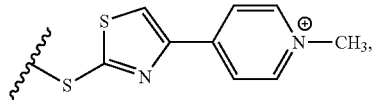

and —CH=CH₂, wherein each occurrence of A is independently an anion, and

X is —OSO₂R₈, wherein R₈ is methyl.

2. The method of claim 1, wherein R₃ is an oxygen protecting group that is a benzyl ether.

3. The method of claim 1, wherein the compound of formula (III) is the compound of formula (III-1):

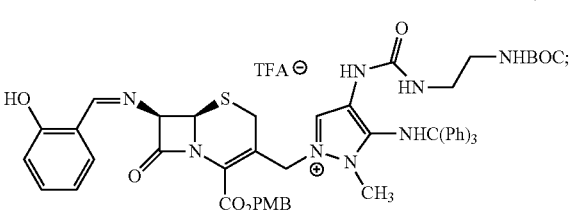

(III-1)

the compound of formula (II) is the compound of formula (II-1):

(II-1)

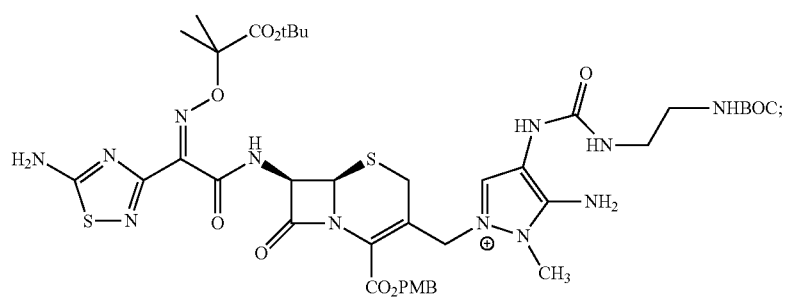

and the compound of formula (IV) is the compound of formula (IV-1):

(IV-1)

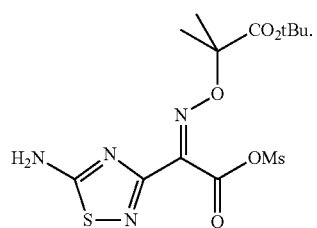

4. The method of claim 3, wherein the compound of formula (IV-1) is prepared from the compound of formula (IVa):

(IVa)

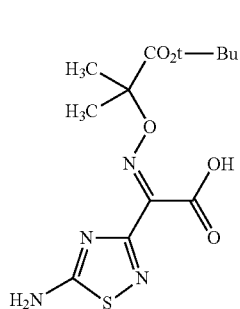

by a process comprising the steps of:
(a) forming a mixture comprising potassium carbonate and the compound of formula (IVa); and (b) adding methanesulfonyl chloride to the mixture of step (a) such that the compound of formula (IV-1) is formed.

5. The method of claim 1, further comprising the step of reacting the compound of formula (II), or a salt thereof, with a strong acid to form a compound of formula (V), or a salt thereof, wherein the compound of formula (V) is selected from the compounds of Table 2.

6. The method of claim 5 wherein the compound of formula (III) has the structure:

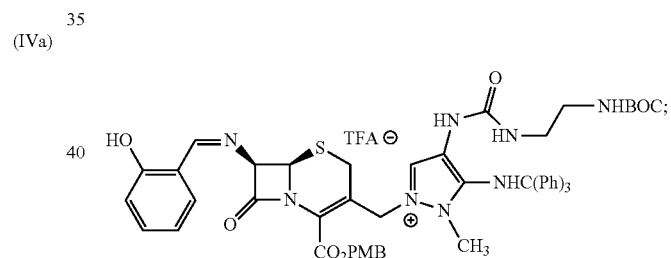

the compound of formula (II) has the structure:

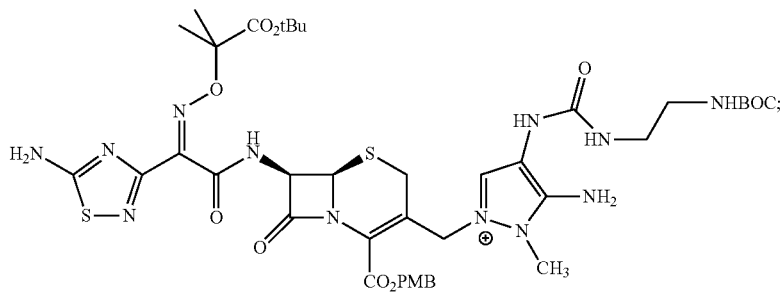

and the compound of formula (V) has the structure:

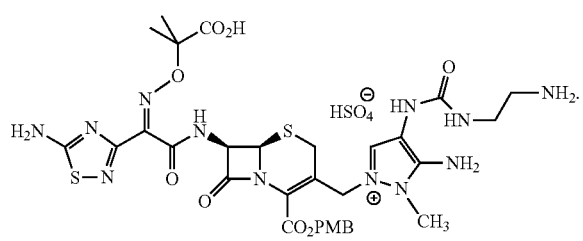

7. The method of claim 5, wherein the compound of formula (III) has the structure:

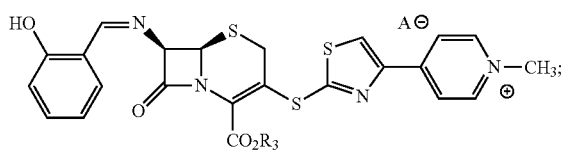

the compound of formula (II) has the structure:

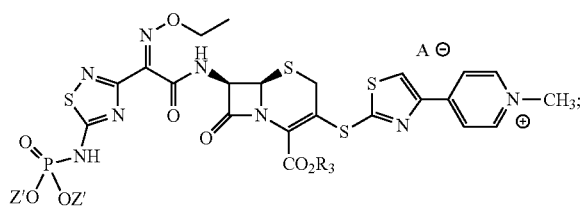

and the compound of formula (V) has the structure:

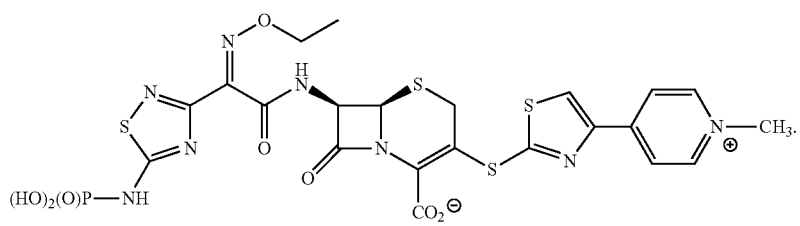

8. The method of claim 5, wherein the compound of formula (III) has the structure:

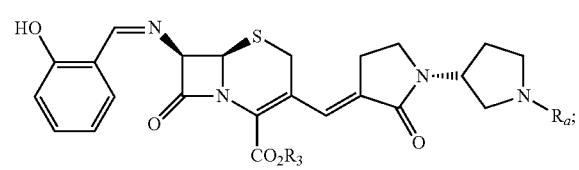

the compound of formula (II) has the structure:

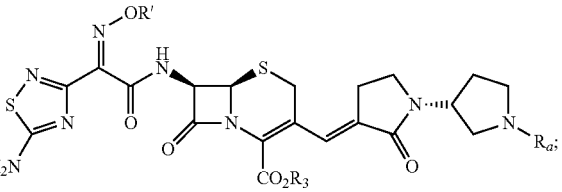

and the compound of formula (V) has the structure:

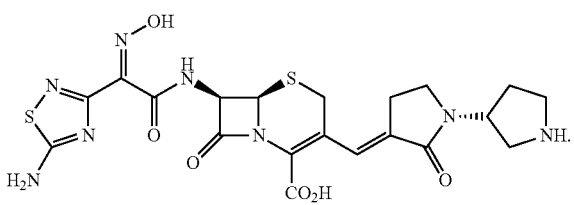

9. The method of claim 5, wherein the compound of formula (III) has the structure:

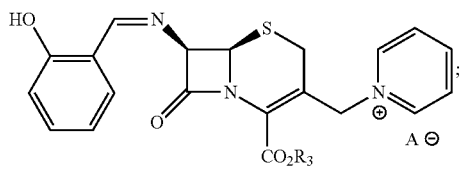

the compound of formula (II) has the structure:

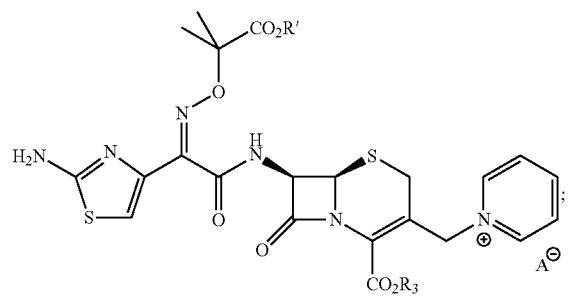

and
the compound of formula (V) has the structure:

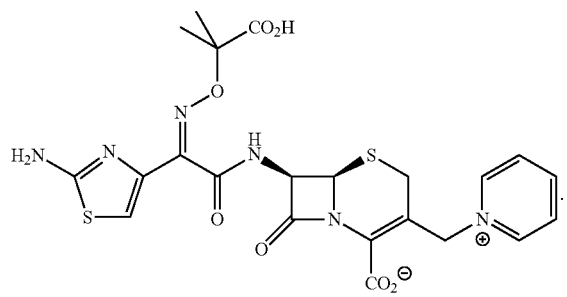

10. The method of claim 5, wherein the compound of formula (III) has the structure:

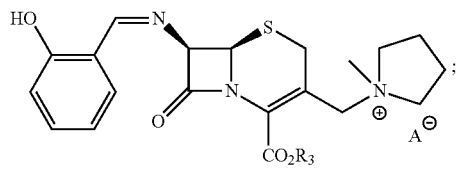

the compound of formula (II) has the structure:

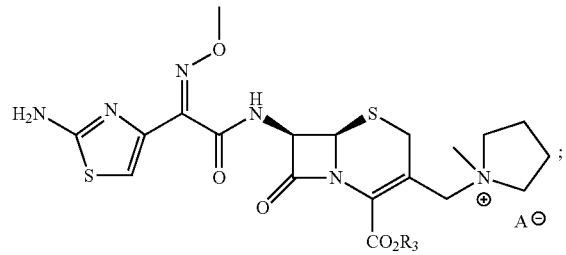

and
the compound of formula (V) has the structure:

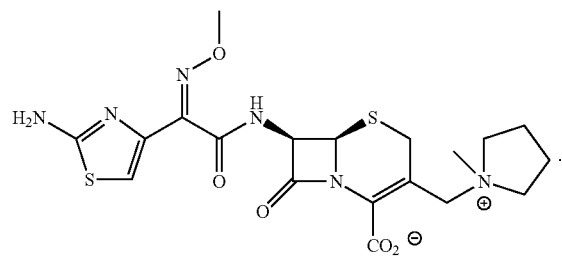

11. The method of claim 5, wherein the compound of formula (III) has the structure:

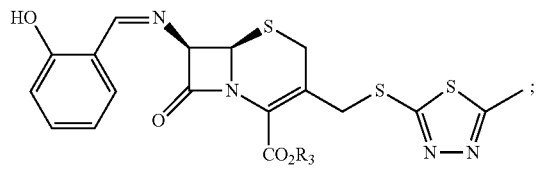

the compound of formula (II) has the structure:

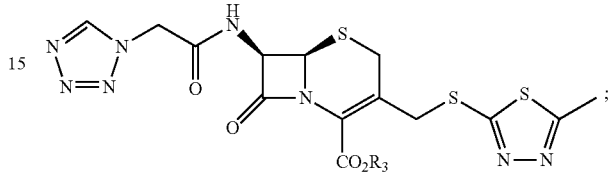

and
the compound of formula (V) has the structure:

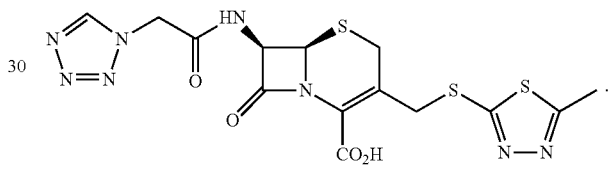

12. The method of claim 5, wherein the compound of formula (III) has the structure:

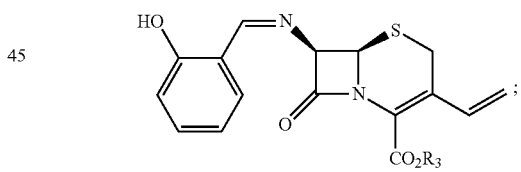

the compound of formula (II) has the structure:

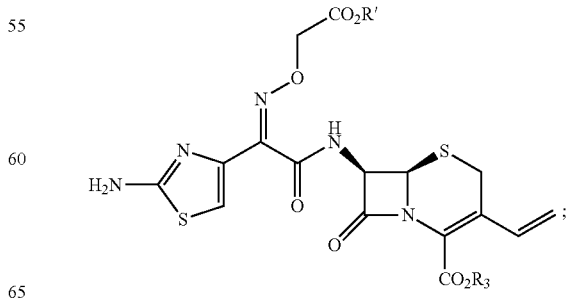

and
the compound of formula (V) has the structure:

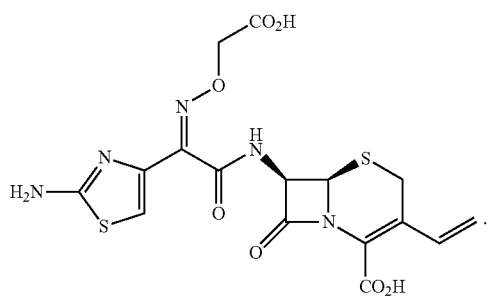 [SMILES: C=CC1=C(C(=O)O)N2C(=O)[C@@H](NC(=O)/C(=N\OCC(=O)O)c3csc(N)n3)[C@H]2SC1]

13. The method of claim 5, wherein the compound of formula (III) has the structure:

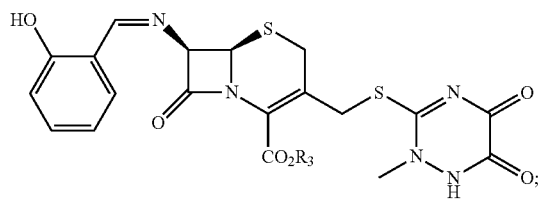

the compound of formula (II) has the structure:

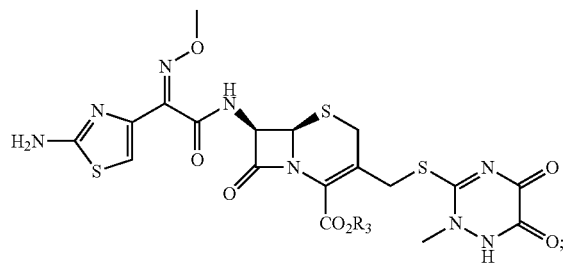

and
the compound of formula (V) has the structure:

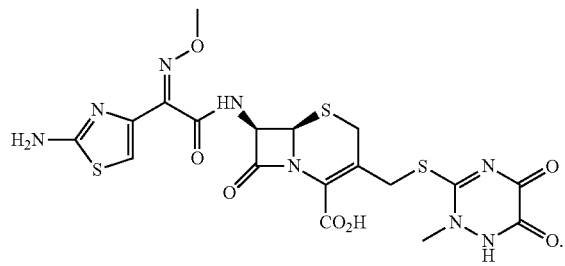 [SMILES: CO/N=C(\C(=O)N[C@@H]1C(=O)N2C(C(=O)O)=C(CSc3nc(=O)c(=O)[nH]n3C)CS[C@H]12)c1csc(N)n1]

14. The method of claim 3, wherein the weight ratio of the compound of formula (III-1) to the compound of formula (IV-1) is 150 g:60 g.

15. The method of claim 3, wherein the organic solvent is dichloromethane; wherein the compound of formula (IV-1) is prepared from the compound of formula (IVa):

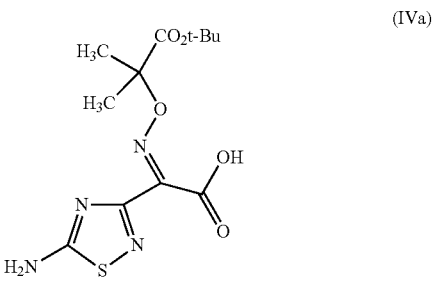 [SMILES: CC(C)(C)OC(=O)C(C)(C)O/N=C(\C(=O)O)c1nsc(N)n1]

by a process comprising the steps of:
(a) forming a mixture comprising potassium carbonate and the compound of formula (IVa); and
(b) adding methanesulfonyl chloride to the mixture of step (a) such that the compound of formula (IV-1) is formed;
wherein the method further comprises the step of reacting the compound of formula (II-1), or a salt thereof, with a strong acid to form a compound of the formula:

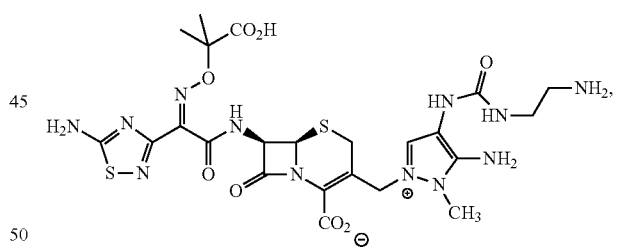

or a salt thereof.

16. The method of claim 1, wherein the compounds of formula (II), formula (III) and formula (IV) are selected from the compounds in Table 1:

TABLE 1

| | Formula (II) | Formula (III) | Formula (IV) |
|---|---|---|---|
| 1 | | | |
| 2 | | | |
| 3 | | | |
| 4 | | | |

TABLE 1-continued

TABLE 1-continued

TABLE 1-continued

| | Formula (II) | Formula (III) | Formula (IV) |
|---|---|---|---|
| 14 | | | |
| 15 | | | |
| 16 | | | |
| 17 | | | |

TABLE 1-continued
| | Formula (II) | Formula (III) | Formula (IV) |
|---|---|---|---|
| 18 |  | 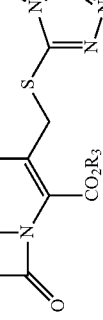 | 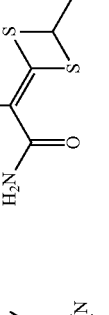 |
| 19 |  | 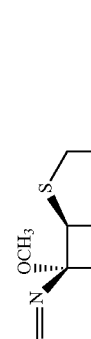 | 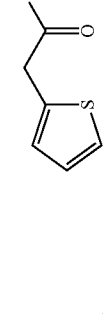 |
| 20 |  | 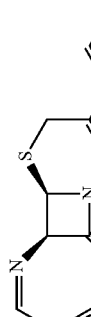 | 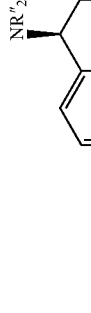 |
| 21 |  | | |

TABLE 1-continued

| | Formula (II) | Formula (III) | Formula (IV) |
|---|---|---|---|
| 22 | | | |
| 23 | | | |
| 24 | | | |

TABLE 1-continued

| | Formula (II) | Formula (III) | Formula (IV) |
|---|---|---|---|
| 25 | | | |
| 26 | | | |
| 27 | | | |

TABLE 1-continued

| | Formula (II) | Formula (III) | Formula (IV) |
|---|---|---|---|
| 28 | | | |
| 29 | | | |
| 30 | | | |

TABLE 1-continued
| | Formula (II) | Formula (III) | Formula (IV) |
|---|---|---|---|
| 31 | 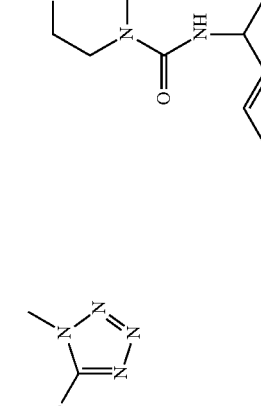 | 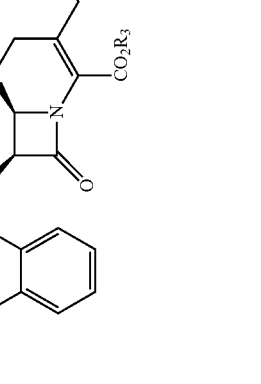 | 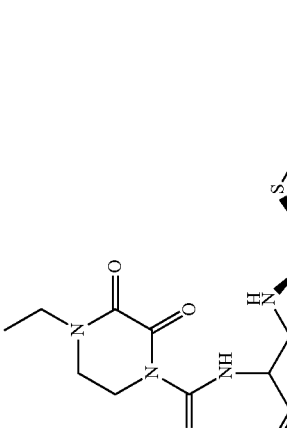 |
| 32 | 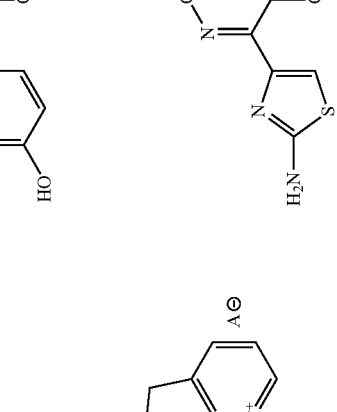 | | |

* * * * *